United States Patent [19]

Young et al.

[11] Patent Number: 5,460,947
[45] Date of Patent: Oct. 24, 1995

[54] APOLIPOPROTEIN B-SPECIFIC MONOCLONAL ANTIBODIES PRODUCED BY TWO NOVEL HYBRIDOMAS

[75] Inventors: Steven Young; Joseph L. Witztum; Linda K. Curtiss, all of San Diego, Calif.

[73] Assignee: The Scripps Research Institute, La Jolla, Calif.

[21] Appl. No.: 219,963

[22] Filed: Mar. 30, 1994

Related U.S. Application Data

[63] Continuation of Ser. No. 415,432, Sep. 27, 1989, Pat. No. 5,330,910, which is a continuation of Ser. No. 893,659, Aug. 6, 1986, abandoned.

[51] Int. Cl.$^6$ .................................................. G01N 33/531
[52] U.S. Cl. .................... 435/7.92; 435/7.9; 435/7.93; 435/7.94; 530/388.25; 436/512; 436/518
[58] Field of Search ........................... 435/7.9, 7.92, 435/7.93, 7.94; 530/388.25; 436/512, 518

[56] References Cited

U.S. PATENT DOCUMENTS

| | | | |
|---|---|---|---|
| 4,376,110 | 3/1983 | David et al. | 435/5 |
| 4,486,530 | 12/1984 | David et al. | 435/7.91 |
| 4,677,057 | 6/1987 | Curtiss et al. | 436/518 |
| 4,722,893 | 2/1988 | Shigeta et al. | 435/7.94 |
| 4,746,605 | 5/1988 | Kerscher et al. | 435/7.1 |
| 4,828,986 | 5/1989 | Smith et al. | 435/7.94 |

FOREIGN PATENT DOCUMENTS

| | | |
|---|---|---|
| WO86/04144 | 7/1986 | WIPO . |
| WO86/05493 | 9/1986 | WIPO . |

OTHER PUBLICATIONS

Albers, et al., *Metabolism* 24: 1339–1351 (1975).
Curry, et al., *Clin Chem.* 24: 280–286 (1978).
Curtiss, et al., *J. Biol. Chem.* 257: 15213–21 (1982).
Curtiss, et al., in *Hybridoma Technology in Bioscience and Medicine*, Plenum Publish., pp. 291–308 (1985).
Hui, et al., *J. Biol. Chem.* 259: 860–69 (1984).
Kodama, et al., *Chem. Abst* 104(10): 75106p (1986).
Kodama, et al., *Chem. Abst.* 104(11): 86986b (1986).
Kohler, et al., *Nature* 256: 495–497 (1975).
Mao, et al., *Biochim. Biophys. Acta* 73: 365–74 (1982).
Mao, et al., *Clin. Chem.* 29: 1890–97 (1983).
Marcel, et al., *J. Biol. Chem.* 257: 13165–13168 (1982).
Maynard, et al., *Clin. Chem.* 30: 1620–24 (1985).
Milne, et al., *Arteriosclerosis* 3: 23–30 (1983).
Patton, et al., *J. Immunol. Meth.* 55: 193–203 (1982).
Patton, et al., *Clin. Chem.* 29: 1898–1903 (1983).
Rosseneu, et al., *Clin. Chem.* 29: 427–433 (1983).
Sevier, et al., *Clin. Chem.* 27: 1797–1806 (1981).
Slater, et al., *Clin. Chem.* 31: 841–845 (1985).
Tikkanen, et al., *Arteriosclerosis* 4: 138–146 (1984).
Tikkanen, et al., *J. Lipid Res.* 23: 1032–38 (1982).
Tsao, et al., *J. Biol. Chem.* 257: 15222–28 (1982).
Watt, et al., *PNAS, USA* 80: 124–128 (1983).
Young, et al., *Arteriosclerosis* 6: 178–188 (1986).
Young, et al., *Chem. Abst.* 105(17): 149039p (1986).
Young, et al., *Chem. Abst.* 104(19): 163931j (1986).
Young, et al., *Clin. Chem.* 32(8): 1484–1490 (1986).
Young, et al., *Clin. Res.* 33: 6A (1985).

*Primary Examiner*—Toni R. Scheiner
*Attorney, Agent, or Firm*—April C. Logan

[57] ABSTRACT

Two hybridomas that produce receptors containing antibody combining sites that immunoreact with apolipoprotein B-100 are disclosed as are uses for the receptors, compositions and diagnostic systems that include the receptors.

19 Claims, 7 Drawing Sheets

APOLIPOPROTEIN B-SPECIFIC MONOCLONAL ANTIBODIES PRODUCED BY TWO NOVEL HYBRIDOMAS

This invention was made with government support under Contract No. HL 14197 awarded by the National Institutes of Health. The government has certain rights in the invention. This is a continuation of U.S. application Ser. No. 07/415,432 filed Sep. 27, 1989, now U.S. Pat. No. 5,330,910 which is a continuation of U.S. application Ser. No. 06/893,659, filed Aug. 6, 1986 (abandoned).

DESCRIPTION

TECHNICAL FIELD OF THE INVENTION

The present invention relates generally to novel hybridomas, and more specifically to hybridomas that produce receptor molecules that immunoreact with apolipoprotein B-100, to the receptor molecules so produced as well as to diagnostic methods and systems employing the receptor molecules.

BACKGROUND OF THE INVENTION

Lipoproteins are the primary carriers of plasma cholesterol and triglycerides. They are micellar lipid-protein complexes that contain protein (referred to as apoprotein) and polar lipids organized in a surface film that surrounds a neutral lipid (triglyceride and cholesteryl ester) core. Lipoproteins were originally identified based on their bouyant densityies as measured by ultracentrifugation. Accordingly there are four major density classes: chylomicrons, very low density lipoproteins (VLDL), low-density lipoproteins (LDL), and high-density lipoproteins (HDL).

Paralleling advances in the technology of ultracentrifugal separations there has been a further subdivision of the LDL and HDL density classes into further subclasses of greater homogeneity. For instance, LDL can be resolved into an intermediate density lipoprotein (IDL) and an $LDL_2$ subclass. However, even these subclasses are composed of functionally heterogeneous populations of lipoprotein particles because of their varied apoprotein content.

Eight major apoproteins, A-I, A-II, A-IV, B, C-I, C-II, C-III, and E, have been isolated, and of the group of minor apoproteins that can be recovered in larger amounts from certain density classes, most can also be found in other density classes. Thus, most LDL particles contain only apo B, however a few particles also contain other apoproteins and this accounts for the trace amounts of apo C-I, apo C-II, C-III, and apo E present in this density class.

In some cases, specific functions have been assigned to particular apoproteins. For instance, a species of apo B synthesized in the liver, termed apo B-100, is recognized and bound by cellular LDL receptors. By binding apo B-100, these receptors bind LDL particles and extract them from the plasma. The LDL is thereby taken into the cells and broken down, yielding its cholesterol to serve each cell's needs. The apo B-LDL receptor interaction thus plays a major role in removal of LDL cholesterol from the bloodstream.

Another species of apo B, termed apo B-48, is not recognized by the LDL receptor. This apo B species, which is only 48 percent as large as apo B-100, is synthesized in humans only by the intestine. Lipoproteins containing apo B-48, such as chylomicrons and chylomicron remnants, do not bind to the LDL receptor.

Although these two species of apo B appear to be under separate genetic controls (a single patient has been described whose body makes apo B-48, but not apo B-100), immunologic studies have demonstrated that apoproteins B-100 and B-48 share antigenic determinants. At least three research groups have reported generation of a total of seven different monoclonal antibodies that bind to either of apo B-100 and apo B-48. The data reported by those researchers strongly suggest that apo B-48 and apo B-100 are structurally related proteins; i.e., that apo B-48 may represent a portion of the apo B-100 protein. Evidence also has been reported that apo B-48 and apo B-100 are not found on the same lipoprotein particle, suggesting that separate apo B particles exist.

Recently, several investigators have suggested that plasma levels of apo B may be more predictive of coronary artery disease (CAD) risk than plasma LDL cholesterol levels. Sniderman et al., Proc. Natl. Acad. Sci. USA 77, 604–608 (1980). Because artherosclerotic vascular disease and its complications continue to be the leading cause of death and debilitation in Western society, there has been a long felt need within the biomedical industry for assay systems capable of identifying individuals at risk for CAD.

Many types of immunoassays for plasma apoprotein B utilizing specific antibody-containing antisera have been reported, including competitive fluid phase and solid phase radioimmunoassays (RIA), enzyme-linked immunosorbant assays (ELISA), radial immunodiffusion assays and others. Problems limiting the widespread application of these apo B immunoassays have been reproducibility, and the quality and specificity of the antisera used. Reviews of the methodological problems of each of the various types of apo B assays are found in Currey et al., Clin. Chem. 24, 280–286 (1978) and Rosseneu et al., Clin. Chem. 28, 427–433 (1983).

Several investigators have reported development of panels of monoclonal antibodies against human apo B for use in studying its antigenic structure and role in lipoprotein metabolism. Furthermore, there have been reports of using anti-apo B monoclonal antibodies to measure plasma apo B levels in fluid-phase RIA's. Patton et al., Clin. Chem. 29, 1898–1903 (1983) and Maynard et al., Clin. Chem. 30, 1620–1624 (1984). In addition, one group has reported use of a mixture of anti-apo B monoclonal antibodies in a radial immunodiffusion assay for plasma apo B. Marconvina et al., Clin. Chim. Acta 147, 117–125 (1985). However, these assay techniques suffer from the necessity of lengthy incubations, repeated centrifugation or use of radioactive materials.

The use of monoclonal antibodies as reagents for assaying for the presence of apo B-100 in human body fluid samples is attractive because once obtained, such reagents can be produced in relatively large amounts with consistent quality. However, there are a number of factors that militate against the use of a particular monoclonal antibody as a component in an apo B-100 assay system.

First, the art teaches that a monoclonal antibody can be too immunospecific to be useful because of the antigenic heterogeneity of its target antigen. For example, the specificity of conventional polyclonal antibody-containing antisera depends on a consensus of hundreds of thousands of different antibodies that bind to antigenic determinants covering most or all of an antigenic protein. As a result, small changes in the structure of the antigen due to genetic polymorphism, heterogeneity of glycosylation or slight denaturation will usually have little effect on polyclonal antibody binding. Similarly, a larger or smaller subset of antibodies from polyclonal antisera will usually bind antigens that have been modified or denatured.

In contrast, monoclonal antibodies usually bind to one antigenic determinant (epitope) on the antigen molecule. If, for any reason, that determinant is altered, the antibody may or may not continue to bind. Whether this is a problem or an advantage depends on the individual circumstances. If, as in the present case, the monoclonal antibody is to be used in a diagnostic assay for an apoprotein, a minor antigenic variation in that protein could cause gross errors.

The antigenic heterogeneity of apoprotein B-100 is well documented. For instance, epitope expression on apo B has been found to be modulated by (1) the composition of the associated lipids, (2) temperature of the immunoreaction, (3) the degree of isolation of LDL from its native environment, and (4) genetic expression between individuals.

Second, because of their unique specificity, the successful use of a monoclonal antibody (MoAb) is often dependent on its affinity for the target antigen. For instance, whereas a MoAb may have sufficient affinity to be useful in binding liquid and solid phase antigen while the MoAb is itself in liquid phase, that same antibody may not be useful as a solid phase-affixed antibody that is useful in binding to and "pulling" the antigen out of solution.

The above problems are generic to the use of monoclonal antibodies. Those skilled in the art have therefore recognized that it is essential to test and characterize monoclonal antibodies in any assay system in which they are to be used. See Goding, James W., *Monoclonal Antibodies: "Principles and Practice."* Pages 40–46, Academic Press, New York (1983).

SUMMARY OF THE INVENTION

One aspect this invention contemplates the hybridoma designated HL130C2.3C5 that has ATCC accession number HB 8746. This hybridoma and its receptor molecules are also referred to herein as MB47.

In another aspect, this invention contemplates receptor molecules that immunoreact with apoprotein B-100 and are secreted by hybridoma ATCC HB 8746.

In still another aspect, this invention contemplates the hybridoma designated V82A6.1G4 that has ATCC accession number HB 8742. This hybridoma and its receptor molecules are also referred to herein as MB24.

Yet another aspect, this invention contemplates receptor molecules that immunoreact with apoprotein B-100 and are secreted by hybridoma ATCC HB 8742.

Another aspect of this invention contemplates a cell culture comprising (a) a hybridoma of this invention; (b) receptor molecules that are secreted by said hybridoma that immunoreact with apoprotein B-100; and (c) a culture medium for the hybridoma.

A further aspect of this invention contemplates a method for assaying a body fluid sample for the presence of apoprotein B-100 comprising the steps of:

(a) providing a body fluid sample to be assayed;

(b) providing receptor molecules in biologically active form that (i) immunoreact with apoprotein B-100, and (ii) are secreted by either hybridoma HB 8746 or hybridoma HB 8742;

(c) admixing the body fluid sample with the receptor molecules;

(d) maintaining the admixture under biological assay conditions for a predetermined time period sufficient for the receptor molecules to immunologically bind apoprotein B-100 present in the sample to form an immunoreactant; and (e) assaying the amount of immunoreactant formed.

In another aspect, this invention contemplates a method for assaying a body fluid sample for apoprotein B-100 comprising the steps of:

(a) providing a body fluid sample to be assayed;

(b) providing a solid support comprised of a solid matrix having affixed thereto in biologically active form a first receptor that immunoreacts with apoprotein B-100 and is secreted by the hybridoma having ATCC accession number HB 8746;

(c) providing a biologically active second receptor that immunoreacts with apoprotein B-100 and is secreted by the hybridoma having ATCC accession number HB 8742, said second receptor linked to an enzyme-label capable of signaling the presence of said second receptor in an immunoreactant;

(d) substantially simultaneously admixing:

(i) the body sample;

(ii) the first receptor; and (iii) the labeled second receptor to form a solid/liquid phase immunoreaction admixture;

(e) maintaining the admixture under biological assay conditions for a predetermined period of time sufficient for the first receptor and the labeled second receptor to immunologically bind apoprotein B-100 present in the sample to form a solid phase sandwich immunoreactant;

(f) separating said solid phase sandwich immunoreactant from the liquid phase; and (g) assaying the amount of labeled second receptor bound in the solid phase sandwich immunoreactant that formed.

In another aspect, this invention contemplates a competitive method for assaying a body fluid sample for apoprotein B-100 comprising the steps of:

(a) providing a body fluid sample to be assayed;

(b) providing a solid support comprised of a solid matrix having a predetermined amount of reagent apoprotein B-100 affixed thereto;

(c) substantially simultaneously admixing (i) the body sample;

(ii) the solid support; and (iii) a predetermined amount of receptor molecules that immunoreact with apoprotein B-100 secreted from either the hybridoma having ATCC accession number HB 8746 or the hybridoma having ATCC accession number HB 8742 to form a solid/liquid phase admixture;

(d) maintaining the admixture under biological assay conditions for a time period sufficient for the receptor molecules to immunologically bind to apoprotein B-100 molecules of the solid support and apoprotein B-100 molecules present in the body fluid sample and form a solid phase immunoreactant and a liquid phase immunoreactant;

(e) separating the solid phase immunoreactant from said liquid phase;

(f) admixing the solid phase immunoreactant with a biologically active second receptor that immunoreacts with the first receptor to form a second solid/liquid phase immunoreaction admixture, the second receptor linked to an enzyme-label capable of signaling the presence of the second receptor in an immunoreactant;

(g) maintaining said second admixture under biological assay conditions for a time period sufficient for the labeled second receptor to immunologically bind to first receptor present as solid phase immunoreactant to form a solid phase sandwich immunoreactant;

(h) separating the solid phase sandwich immunoreactant from the liquid phase; and (i) assaying the amount of labeled second receptor bound in said solid phase sandwich immunoreactant.

In another aspect, this invention contemplates a cell culture comprising:

(a) the hybridoma having ATCC accession number HB 8746;

(b) receptor molecules secreted by the hybridoma that immunoreact with apoprotein B-100; and (c) a culture medium for the hybridoma.

In another aspect, this invention contemplates a composition comprising:

(a) the hybridoma having the ATCC accession number HB 8742;

(b) receptor molecules secreted by the hybridoma that immunoreact with apoprotein B-100; and (c) a culture medium for the hybridoma.

In another aspect, this invention contemplates a diagnostic system for assaying for the amount of apo B-100 in a body sample comprising:

(a) a biologically active first specific binding agent that comprises receptor molecules that (i) immunoreact with apoprotein B-100; and (ii) are either the receptor molecules secreted by hybridoma ATCC HB 8746 or the receptor molecules secreted by hybridoma ATCC HB 8742; and (b) a biologically active labeled second specific binding agent for signaling the immunoreaction of the first binding agent with apo B-100.

A solid matrix affinity sorbant comprised of a solid phase matrix affixed to biologically active receptor molecules that immunoreact with apoprotein B-100 and are selected from the group consisting of:

(a) the receptor molecules secreted by hybridoma HB 8746;

(b) the receptor molecules secreted by hybridoma ATCC HB 8742; and (c) a mixture of the receptor molecules from (a) and (b).

The present invention provides several benefits and advantages.

One benefit of the present invention is that the hybridomas of the present invention can be used to produce in relatively large amounts with consistent quality receptors that immunoreact with apo B-100.

Another benefit of the present invention is that the receptors of this invention are useful, inter alia, for assaying for the amount of cholesterol carrying apo B-100 in a body fluid sample.

One advantage of the present invention is that the receptors of this invention can be used in enzyme linked immunosorbant assays for apo B-100 in formats that do not require centrifugation procedures.

Another advantage is that the assay methods of this invention can be completed in relatively short time periods.

Other advantages and benefits of the present invention will become readily apparent to those skilled in the art from the following description of the invention, the drawings and the appended claims.

BRIEF DESCRIPTION OF THE DRAWINGS

FIG. 1A illustrates that monoclonal MB24 immunoreacts with apo B-100 and apo B-48 from VLDL (V) and chylomicrons (C). FIG. 1B illustrates monoclonal that MB47 immunoreacts with apo B-100 from V and C but not with apo B-48 from either V or C. FIG. 1C is a negative control showing that a monoclonal antibody specific for sheep red blood cells does not immunoreact with any antigen present. FIG. 1D is another negative control showing that an immunopurified polyclonal antiserum to phenyl-beta-O-glucoside does not recognize any antigens present. Panel 1E is a positive control showing that an immunopurified rabbit polyclonal antiserum against human LDL-apoprotein recognizes both apo B-100 and apo B-48 in both V and C.

LDL was prepared from pooled plasma of 10 subjects ( - - - - ) or from one normolipidemic subject (__). Plasma was obtained by plasmapharesis of subjects following an approximately twelve-hour fasting period.

Figure 3:
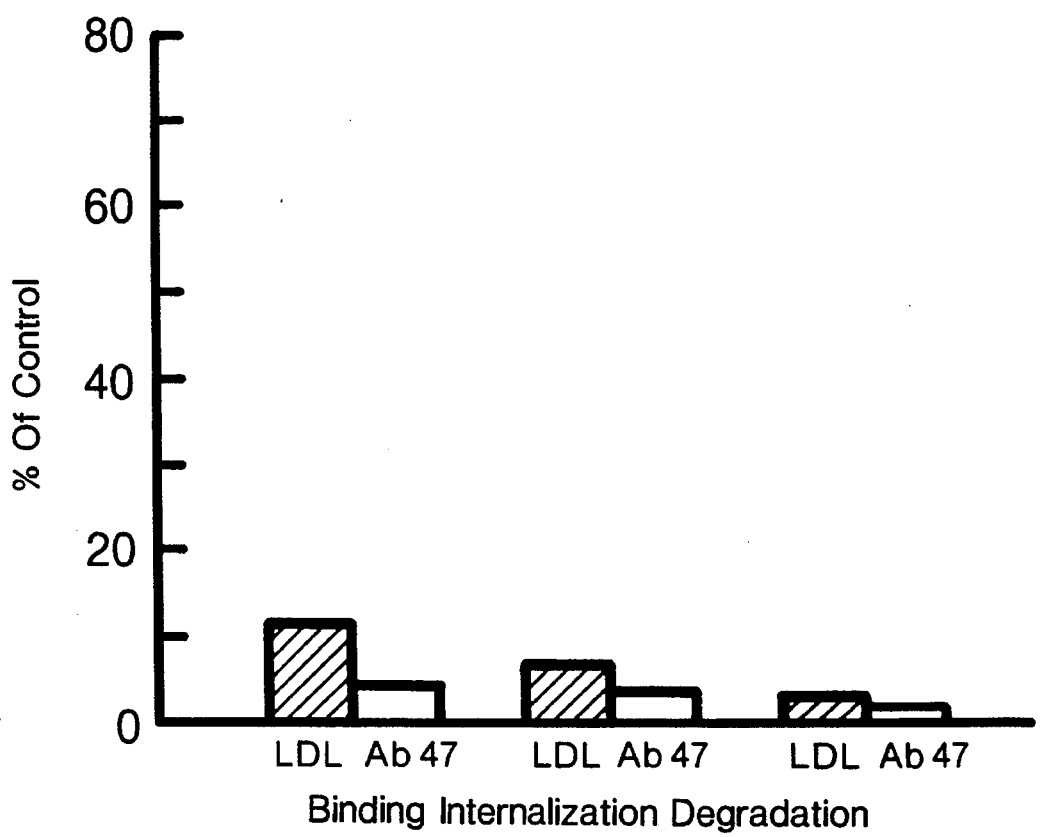

FIG. 3 is a bar graph showing the degree of inhibition by antibody MB47 (open bars: MB47) and excess unlabeled human LDL (hatched bars: LDL) of $^{125}$I-human LDL binding, internalization and degradation by cultured human fibrobalsts. Fibroblast monolayers were grown in 35 millimeter wells in DME containing 10 percent fetal calf serum.

Fibroblast LDL-receptors were stimulated by approximately 24 hours of preincubation of the fibroblasts with growth medium containing 2.5 milligrams per milliliter (mg/ml) lipoprotein-depleted serum (LDS) (DME-LDS). DME-LDS containing 2.5 micrograms per milliliter (ug/ml) $^{125}$I-LDL and either 20 percent MB47 hybridoma culture supernatant (v/v) or a 200-fold excess of unlabeled LDL (final concentration, 500 ug/ml) were admixed and maintained (incubated) for about 16 hours at 4 degrees C. prior to being placed on the fibroblast monolayers.

Determination of binding, internalization, and degradation were performed in triplicate, and are expressed as a percentage of control values that were determined in the absence of monoclonal receptor MB47. Inhibition of specific binding, internalization, and degradation by monoclonal receptor MB47 was comparable to that produced by a 200-fold excess of unlabeled LDL.

Figure 4A:
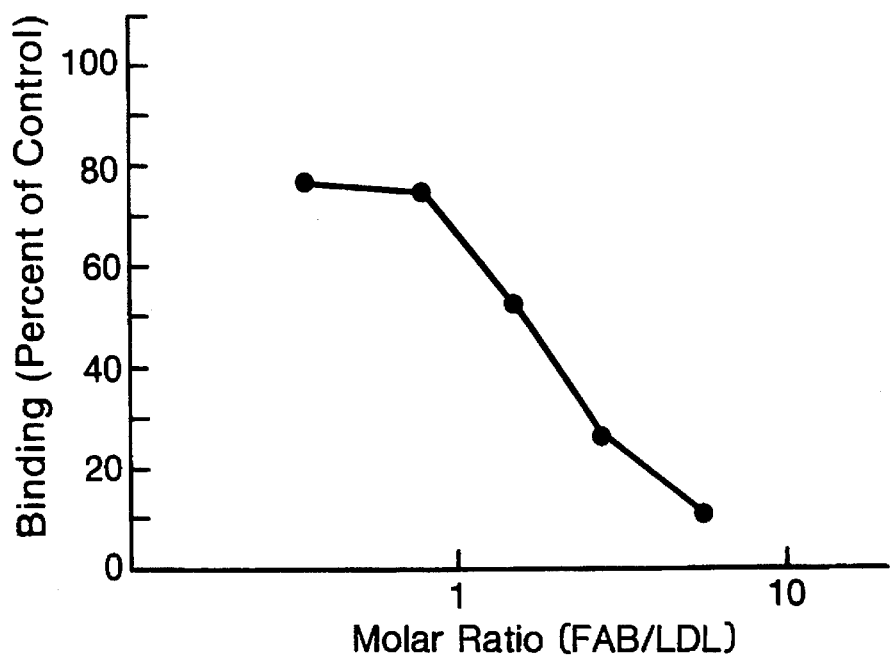
Figure 4B:
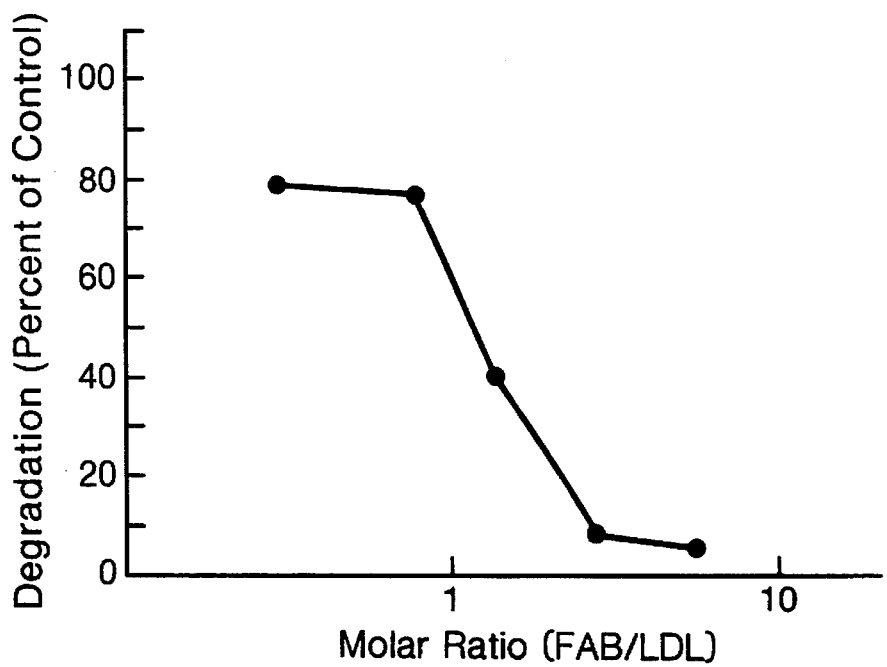

FIG. 4 contains two graphs showing the ability of monovalent Fab fragments of monoclonal antibody MB47 to inhibit $^{125}$I-human LDL binding and degradation by human fibroblasts. Individual media containing increasing amounts of MB47-Fab fragments and a constant amount of $^{125}$I-LDL (2.5 um/ml) were admixed and maintained (incubated) for a time period of about 15 hours at 4 degrees C. prior to being placed on the fibroblast monolayers. The Fab concentration is expressed as the molar ratio of Fab/LDL present in each medium (assuming a molecular weight (MW) of Fab to be 40,000 daltons and a molecular weight of apo B to be 550,000 daltons).

Binding and degradation are expressed as the precentage of control values in the absence of MB47-Fab fragments. All determinations were performed in duplicate. Excess unlabeled LDL (final concentration, 500 ug/ml) produced greater than 95 percent inhibition of $^{125}$I-LDL binding (Panel A) and degradation (Panel B). Similar results were obtained in three studies with different Fab preparations of monoclonal receptor MB47.

Figure 5A:
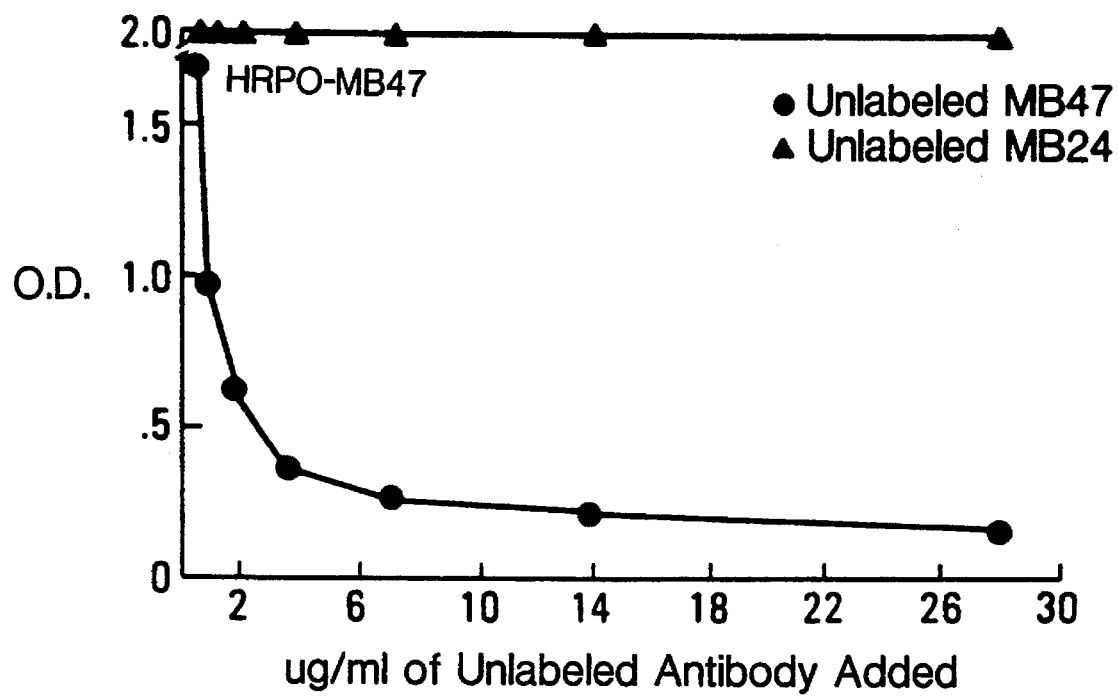

FIG. 5 contains two graphs. FIG. 5A illustrates the ability of a known, constant amount of horse radish peroxidase-labeled MB47 (HRPO-MB47) receptors to immunoreact with solid phase affixed reagent apo B-100 in the presence of increasing amounts of MB24 receptor molecules. The ordinate is in relative optical density units while the abscissa is in units of micrograms per milliliter of unlabeled antibody protein added as (ug/ml) competitor.

A constant amount (20 ug) of HRPO-coupled MB47 receptors was substantially simultaneously admixed with increasing amounts of unlabeled MB47 (●) or unlabeled MB24 (▲) receptors and solid phase-affixed reagent apo B-100 (LDL). The admixtures were maintained for 3 hours at 25 degrees C. thereby allowing the receptors to immunologically bind the reagent apo B-100 and form a solid phase immunoreactant. The amount of solid phase-bound labeled MB47 was then assayed as in the competition ELISA described in the Materials and Methods section.

FIG. 5A illustrates that the presence of increasing amounts of unlabeled MB47 receptors in the immunoreaction admixture correspondingly decreases the amount of labeled MB47 receptors bound as solid phase immunoreactant. Thus, unlabeled MB47 competes with labeled MB47 for LDL.

On the other hand, FIG. 5A also illustrates that increasing amounts of unlabeled MB24 receptors do not significantly decrease the amount of labeled MB47 bound as solid phase immunoreactant. Thus, unlabeled MB24 does not compete with labeled MB47 for binding to LDL.

Figure 5B:
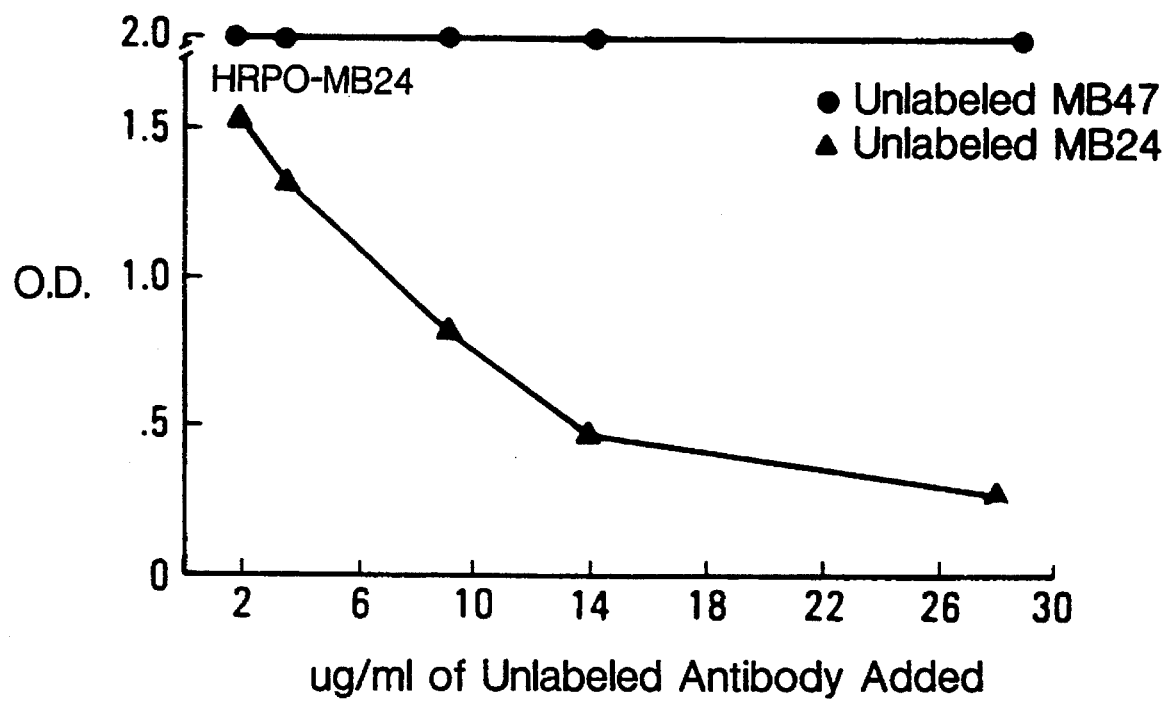

FIG. 5B illustrates that similar results are obtained using HRPO-labeled MB24 receptors and unlabeled MB47 receptors. MB47 and MB24 receptors therefore bind to different epitopes that are sufficiently separated on the surface of apo B-100 so as to allow binding of both receptors to a single apo B-100 molecule without sterically competing with and inhibiting binding.

Figure 6A:
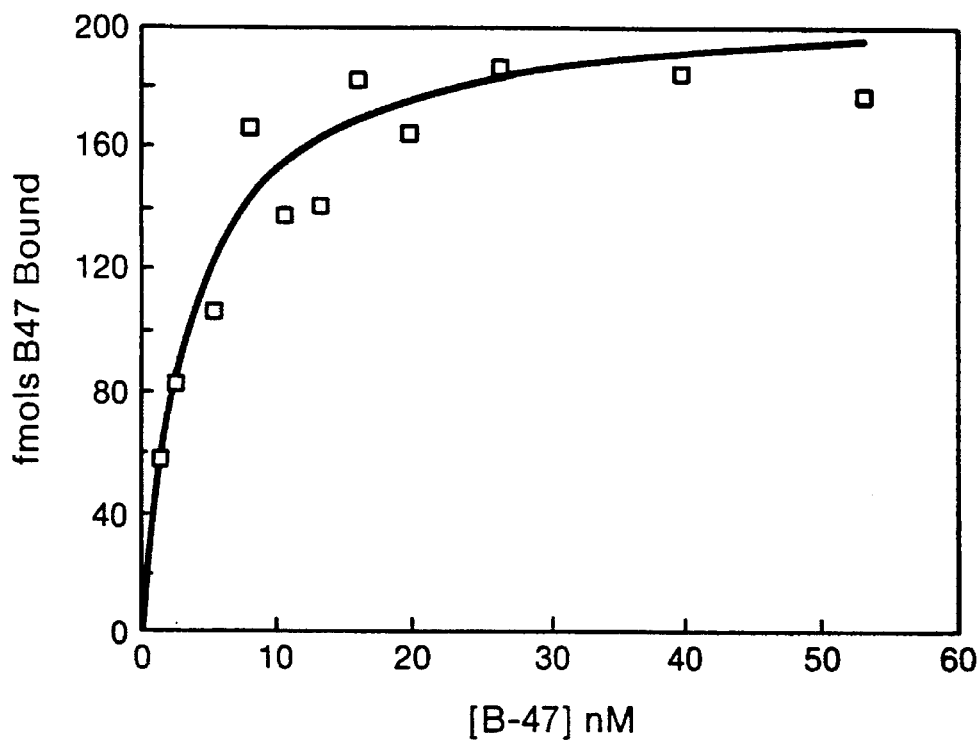

FIG. 6 contains two graphs. FIG. 6A represents the binding of $^{125}$I-labeled B-47 to LDL in a fluid phase RIA. The ordinate is in units of femtomoles (fmols) bound whereas the abscissa is in units of nanomoles (nM) of the antibody admixed.

Immunopurified monoclonal antibody MB47 was iodinated with $^{125}$I using the Iodogen technique to a specific activity of 3000 counts per minute per nanogram (cpm/ng). Following extensive dialysis against phosphate-buffered saline (PBS), over 95 percent of the radioactivity was precipitable by 10 percent trichloroacetic acid (TCA). Greater than 98 percent of the $^{125}$I-MB47 bound to a LDL column. Assays were performed in triplicate in 10×75 millimeter (mm) silicone-coated glass tubes. Increasing concentrations of $^{125}$I-MB47 in 0.1 ml of bovine serum albumin-barbital (BSA-barbital) buffer (pH value 8.0) were added to 100 ng of pooled, normolipidemic human LDL diluted in 0.2 ml of BSA-barbital buffer. Each tube contained 182 fmoles of LDL apo B (assuming an apo B molecular weight of 550,000 daltons).

After incubation (admixture and maintenance) for a time period of 16 hours at 4 degrees C., LDL was quantitatively precipitated by a lipoprotein-depleted rabbit antiserum specific for human LDL. [Only the fraction of the rabbit antiserum having a density (d) greater than 1.21 g/ml was used because monoclonal antibody MB47 binds rabbit apolipoprotein B.]

Preliminary studies established a concentration of delipidated rabbit antiserum that precipitated greater than 98 percent of 100 ng of $^{125}$I-human LDL. After addition of the rabbit antiserum, the tubes were incubated for about 16 hours at 4 degrees C.

The supernatants were removed, and the pellets were washed twice with 2 ml of ice cold barbital buffer (pH value 8.0). Nonspecific binding and precipitation were determined in two sets of parallel tubes. In the first set, no human LDL was added to the initial incubation, but the same amount of rabbit second antibody was added. In the second set of tubes, nonimmune rabbit serum (d greater than 1.21 mg/ml fraction) was substituted for the immune rabbit serum antibody.

Both methods yielded substantially identical values for nonspecific binding, which was linear with increasing concentrations of $^{125}$I-MB47 monoclonal antibody, and in all cases was less than 1 percent of the total counts added. Specific $^{125}$I-MB47 binding to LDL was obtained by subtracting nonspecific binding from total binding. Binding data were analyzed utilizing a linear regression program for Scatchard analysis of ligand binding systems, which provided an estimate of the antibody affinity constant (Ka) and the receptor or epitope concentration.

Figure 6B:
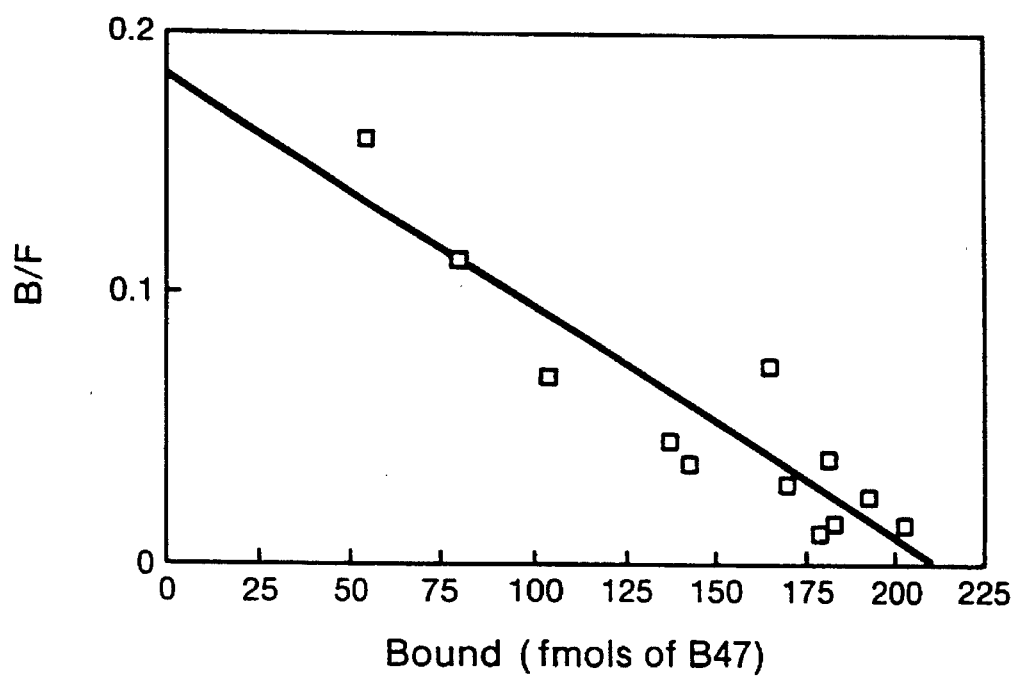

The Ka of $^{125}$I-MB47 for LDL was thereby determined to be $3.82 \times 10^9 M^{-1}$. Extrapolation of the line to conditions of infinite antibody excess yielded an estimate of 212 fmols (35 ng) of $^{125}$I-MB47 bound by 182 fmoles (100ng) of LDL when the molecular weight of apo B is assumed to be 550,000 daltons. These data are shown in FIG. 6B of this Figure wherein the ordinate is in units of the ratio of bound (B) to free (F) (B/F) antibody, whereas the abscissa is in units of fmoles of bound antibody (fmols of MB47).

Figure 7:
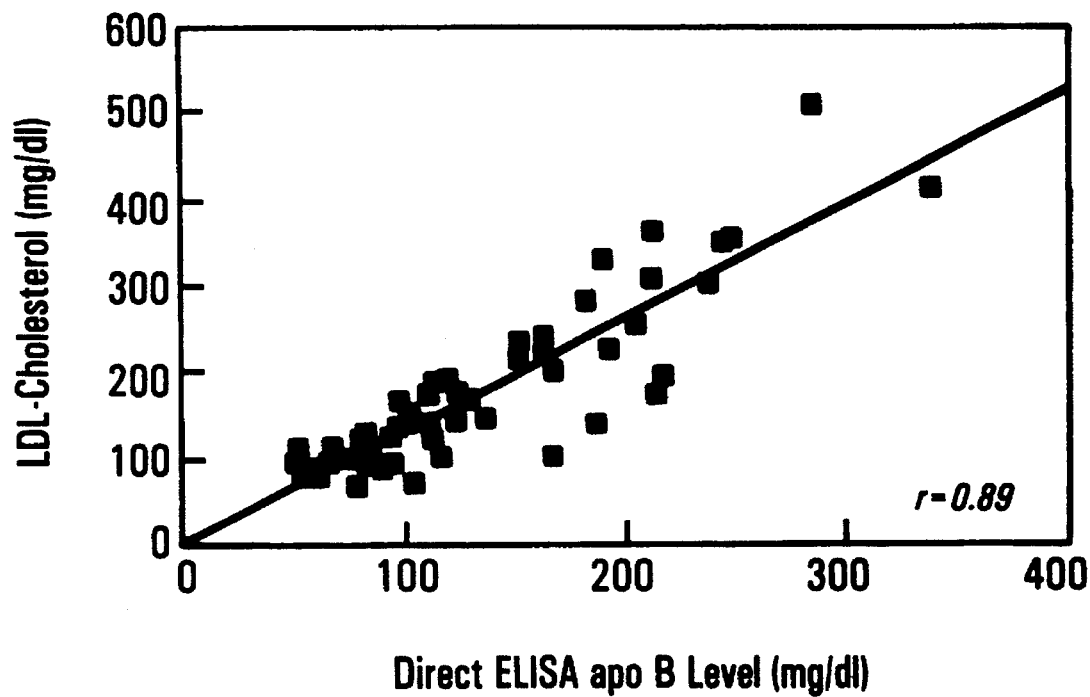

FIG. 7 illustrates the correlation between the mg of LDL-cholesterol per deciliter (dl) of sample determined by *Lipid Research Clinic Procedures*, HEW Publication No. 75-628 (NIH), 2nd ed., Wash., D.C. Gov. Print. Off. (1974), and mg of apo B-100 per dl of sample determined using the non-competitive ELISA described in the materials and methods section.

The correlation coefficient, r=0.89, determined by the Spearman Rank Correlation test for non-parametric data [Sokal et al., *Biometry*, 2nd ed., W. H. Freeman Co., San Francisco, Calif., 561–616 (1981)], indicates a significant correlation between the levels of apo B-100 determined by the non-competitive ELISA described herein and the LDL-cholesterol levels in 60 human plasma sampels.

Figure 8:
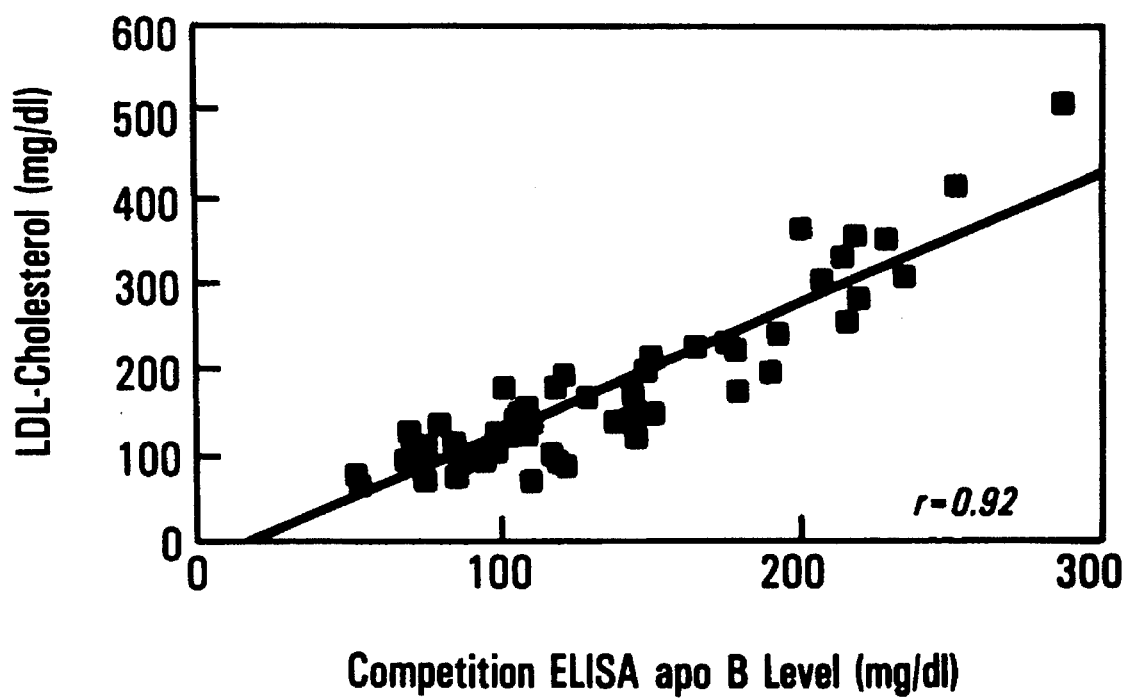

FIG. 8 is similar to FIG. 7 and illustrates a significant correlation, r=0.92, between the levels of apo B-100 as determined by a competition ELISA method of this invention and the LDL-cholesterol levels in the same 60 human samples.

Figure 9:
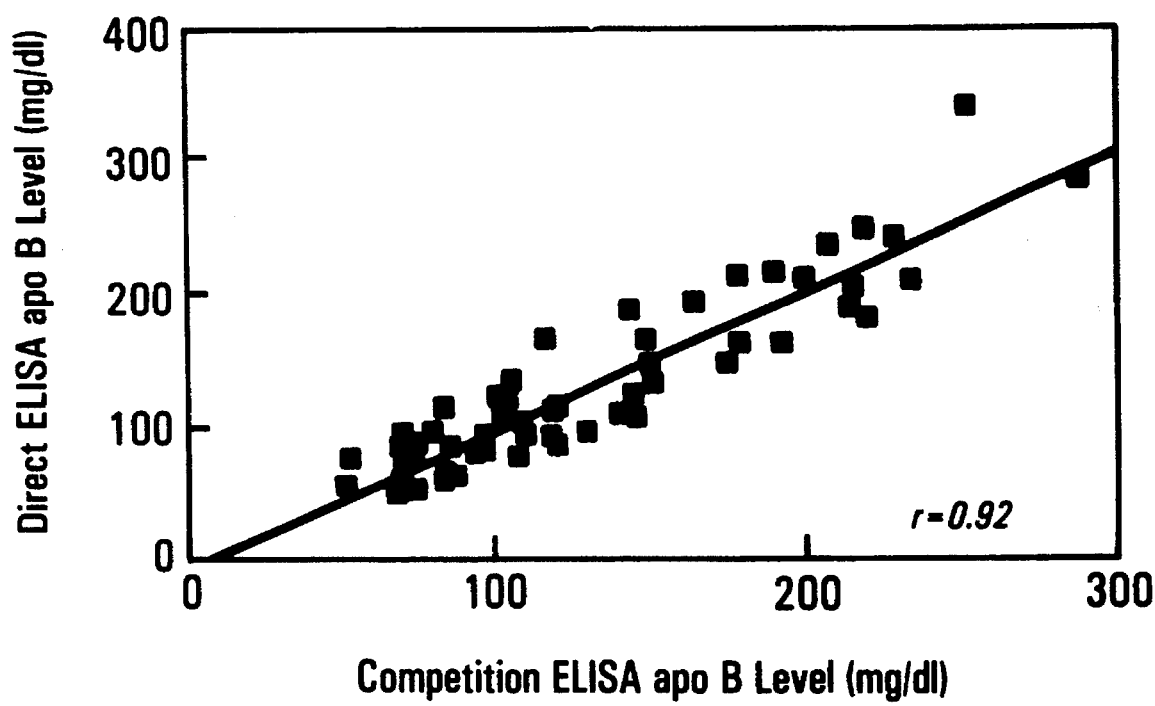

FIG. 9 illustrates the significant correlation, r=0.92, as determined by the Spearman Rank Correlation test, between the results obtained using the non-competitive ELISA (ordinate) and the competitive ELISA (abscissa) on the same 60 human samples used in FIGS. 7 and 8.

DETAILED DESCRIPTION OF THE INVENTION

I. General Discussion

A. Definitions

The term "antibody" refers to a receptor molecule that is a member of a family of glycosylated proteins called immunoglobulins, which can specifically combine with an antigen.

An "antibody combining site" is that structural portion of an antibody molecule comprised of heavy and light chain variable and hypervariable regions that specifically binds antigen.

The word "antigen" has been used historically to designate an entity that is bound by an antibody, and also to designate the entity that induces the production of the antibody. More current usage limits the meaning of antigen to that entity bound by an antibody, while the "immunogen" is used for the entity that induces antibody production. Where an entity discussed herein is both immunogenic and antigenic, it will generally be termed an antigen.

"Antigenic determinant" refers to the actual structural portion of the antigen that is immunologically bound by an antibody combining site. The term is also used interchangeably with "epitope".

The term "biologically active" refers at least to the ability to specifically bind ligand or specific binding agent although other general or effector capability can also be present.

The word "complex" as used herein refers to the product formed when a specific binding agent binds to a target ligand. Exemplary complexes are immunoreactants, protein A bound to an antibody and the like.

"ELISA" refers to an enzyme-linked immunosorbent assay that employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and No. 4,016,043, which are all incorporated herein by reference.

"Enzyme" refers to a protein capable of accelerating or producing by catalytic action some change in a substrate for which it is often specific.

"Epitope" refers to that portion of a molecule that is specifically recognized by an antibody combining site. It also is referred to as the determinant or antigenic determinant.

"Idiotopes" or "idiotypic determinants" are antigenic determinants on the variable and hypervariable portions of an antibody molecule that can be recognized by a combining site of other antibodies. Idiotopes are usually divided into two types, those that are binding site-associated determinants and those that are non-binding site-associated. The collection of idiotpes on an antibody molecule constitutes its idiotype. It is believed that an antibody combining site produced by a hybridoma possesses a single, unique set of idiotopes; i.e., a unique antibody combining site idiotype.

"Immunoreactant" as used herein refers to the product of an immunological reaction; i.e., that entity produced when a ligand is immunogically bound by a receptor molecule. An "immunoreactant" is a particular type of "complex".

The word "isolated" as used herein in relation to receptor molecules means that substantially only one species of antibody combining site is present.

The terms "labeling means", "indicating group" or "label" are used interchangeably herein to include single atoms and molecules that are either directly or indirectly involved in the production of a detectable signal to indicate the presence of a immunoreactant. Any labeling means can be linked to or incorporated in a receptor or used separately, and those atoms or molecules can be used alone or in conjunction with additional reagents. Such indicating groups or labels are themselves well-known in immunochemistry and constitute a part of this invention only insofar as they are utilized with otherwise novel receptors, methods and/or systems.

"Ligand" refers to a molecule that contains a structural portion that is bound by a specific receptor, e.g., an antigen that is bound by a receptor.

The term "receptor" is used herein to indicate a biologically active molecule that immunologically binds to (or with) an antigen. Such binding typically occurs with an affinity of about $10^5$ to about $10^{10}$ liters per mole ($M^{-1}$) and is a specific interaction of the epitope of the antigen with the antibody combining site of the receptor.

A receptor molecule of the present invention is any intact antibody, substantially intact antibody or an antibody combining site idiotype-containing polypeptide portion of an antibody (e.g., an Fab fragment) such as in ascites fluid or tissue culture supernatant.

The word "receptor" is also used herein for molecles on cell surfaces that bind other molecules. Cell surfaces receptors are always denominated herein with the name of the bound entity preceding the word "receptor" to avoid any ambiguity. An exemplary cell surface "receptor" is the previously described LDL receptor.

Biological activity of a receptor molecule is evidenced by the immunologic reaction of the receptor with its antigenic ligand upon their admixture in an aqueous medium to form an immunoreactant, at least at physiological pH values and ionic strengths. Preferably, biological activity occurs under biological assay conditions; i.e., those conditions wherein the receptor molecules of this invention bind to the antigenic ligand within a pH value range of about 5 to about 9, at ionic strengths such as that of distilled water to that of about one molar sodium chloride, and at temperatures of about 4 degrees C. to about 45 degrees C. All of the receptor molecules described herein were biologically active.

Antibody combining site idiotype-containing polypeptide portions (antibody Combining sites) of antibodies are those portions of antibody molecules that contain the combining site idiotopes and bind to the ligand, and include the Fab, Fab', F (ab')$_2$ and F(v) portions of the antibodies. Fab and F(ab')$_2$ portions of antibodies are well known in the art, and are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and then alkylation of the resulting protein mercaptan with reagent such as iodoacetamide. Intact antibodies are preferred, and along with Fab portions are utilized as illustrative of the monoclonal receptor molecules this invention.

The words "secrete" and "produce" are often used interchangeably in the art as to cells from which antibody molecules are obtained. Cells that produce antibodies may, however, not secrete those molecules into their environment. The hybridoma cells of interest herein secrete monoclonal antibodies into their environment. Nevertheless, such cells are often referred to herein as "antibody-producing" cells, and their antibodies are referred to as being "produced" in keeping with the phrase utilized in the art.

The term "specific binding agent" as used herein refers to a molecular entity capable of selectively binding a ligand. Exemplary specific binding agents are receptors, complement fragments, protein A and the like.

The phrase "substantially pure"0 as used herein in relation to receptor molecules means that, within detectable limits, only one species of antibody combining site is present as an effective binding agent for apo B-100. Thus, while a substantially pure receptor molecule preparation can contain more than one species of antibody combining site, such a preparation displays a single binding affinity for apo B-100. For instance, tissue culture supernatants produced by a hybridoma of this invention typically contain myeloma proteins as well as receptors of this invention. A receptor molecule in substantially pure form is typically designated a "monoclonal antibody" by those skilled in the art because such compositions are produced using monoclonal hybridoma cultures.

The phrase "substantially simultaneously" as used herein in relation to the admixture of 3 or more antigen and receptor components to form an immunoreaction admixture means that all components are present and admixed in a single admixture within about 15 minutes and preferably within about 5 minutes of the admixture of any 2 of the components.

B. Hybridomas and Monoclonal Receptors

The present invention contemplates a hybridoma, having the laboratory designation HL130C2.3C5, that produces receptor molecules that:

(a) immunoreact with a conserved antigenic determinant on apoprotein B-100;

(b) competitively inhibit the binding of apoprotein B-100 to LDL receptor; and (c) have an affinity constant for LDL of about $3.82 \times 10^9 M^{-1}$ in a fluid phase competitive equilibrium radioimmunoassay (RIA). These receptor molecules are usually referred to as MB47.

The present invention also contemplates a hybridoma, having the laboratory designation V82A6.1G4, that produces receptor molecules that immunoreact with an apoprotein B-100 antigenic determinant and have an affinity constant for LDL of about $3.0 \times 10^9 M^{-1}$ in a solid phase competitive equilibrium RIA. These receptor molecules are usually referred to as MB24.

Hybridomas HL130C2.3C5 and V82A6.1G4 were deposited with the American Type Culture Collection (ATCC), Rockville, Md. on Mar. 6, 1985 under the following ATCC accession numbers:

| Hybridoma | Receptor Designation | ATCC Accession No. |
|---|---|---|
| V82A6.1G4 | MB24 | HB 8742 |
| HL130C2.3C5 | MB47 | HB 8746 |

The above ATCC deposits were made in accordance with the Budapest Treaty on the International Recognition of the Deposit of Microorganisms for the Purposes of Patent Procedure.

The hybridomas of the present invention were formed by fusing an antibody-producing cell and a myeloma cell line. Such receptor producing cells were first described by Kohler and Milstein, *Nature*, 256, 495 (1975), which description is incorporated herein by reference. Receptors are typically obtained from the supernatants of hybridoma cell cultures, preferably monoclonal cell cultures, or, alternatively, from ascites fluid or other body fluids obtained from non-human, warm-blooded host animals, preferably those that are histocompatible or immunocompromised, into which the hybridoma cells were introduced and cultured.

Thus, in another embodiment, the present invention contemplates a cell culture comprising (a) a hybridoma of this invention; (b) receptor molecules that are secreted by the hybridoma that immunoreact with apoprotein B-100; and (c) a culture medium for the hybridoma. Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8,396 (1959)) supplemented with 4.5 gm/l glucose, 20 mm glutamine, and 20 percent fetal calf serum. An exemplary inbred mouse strain is the Balb/c.

In still another embodiment, the present invention contemplates the receptors, designated MB47 and MB24, that are produced by the hybridomas designated HB 8746 and HB 8742 respectively, and immunoreact with apoprotein B-100. Thus, a receptor of this invention can be prepared by culturing in a suitable medium an appropriate hybridoma of this invention and recovering the receptor from the medium.

Previously, Curtiss et al., *J. Biol. Chem.*, 257, 15213 (1982), reported production and characterization of 11 apo B specific receptor molecules, including that designated MB24 produced by hybridoma HB 8742. Hybridoma HB 8742 was obtained, as described in more detail in the Materials and Methods section, by fusing splenocytes of mice immunized with human VLDL.

The IgG fraction of MB24 containing ascites fluid generated from intraperitoneal growth of HB 8742 was characterized by isoelectric focusing (IEF). As noted in Curtiss et al., supra, the fusion was performed with P3×63 Ag8 myeloma cells that secrete an $IgG_1k$ immunoglobulin. Therefore, upon IEF, HB 8742 ascites fluid demonstrated a unique pattern of multiple protein bands representing randomly mixed heavy and light chain-containing immunoglobulin molecules in addition to the P3×63 Ag8 myeloma $IgG_1k$ antibody and receptor MB24.

Hybridoma HB 8746 produces MB47 receptor molecules and was formed by fusing splenocytes of mice immunized with LDL and P3×63 Ag8.653.1 myeloma cells. This variety of the parent myeloma does not secrete a myeloma protein. IEF of HB 8746 ascites fluid reveals a unique pattern of protein bands representing the IgG2a heavy and kappa light chains. Thus, both hybridomas of this invention can be characterized in part by the IEF pattern of the receptor molecules they produce.

While the V82A6.1G4 hybridoma of this invention produces more than one type of receptor molecule, the receptor molecules of this invention can be easily identified and isolated by their individual abilities to immunoreact with apo B-100 antigenic determinants. The antigenic specificities of MB24 and MB47 were examined by assaying their individual abilities to immunoreact with apoproteins obtained from chylomicrons, VLDL, LDL and HDL in the Western blot assay described hereinbelow.

Figure 1:
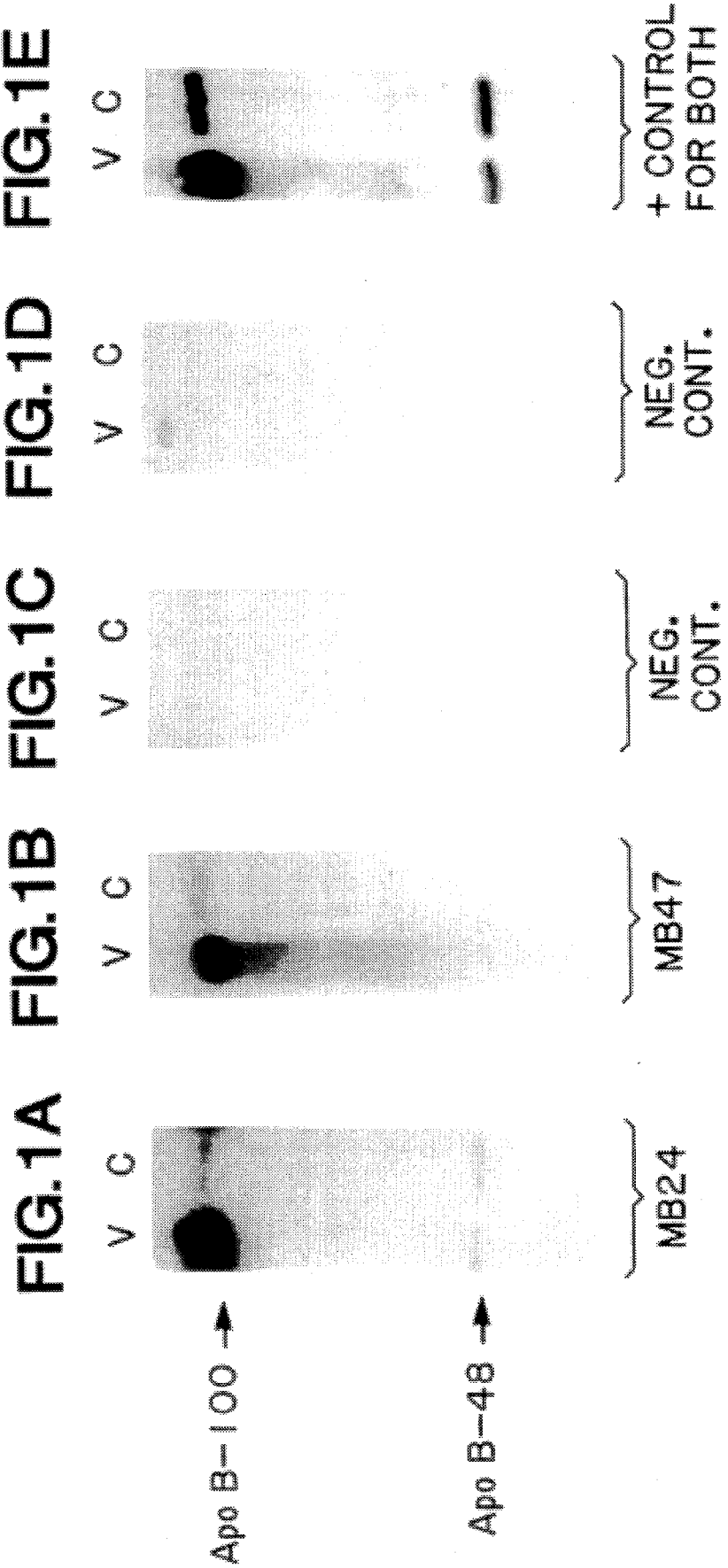
FIGS. 1A, 1B, 1C, 1D and 1E represent a photograph of a Western Blot assay autoradiograph wherein the ability of MB47 and MB24 receptor molecules to immunoreact with apo B-100 and apo B-48 obtained from delipidated chylomicrons and VLDL is demonstrated. VLDL and chylomicrons were delipidated and subjected to SDS-polyacrylamide gel electrophoresis (SDS-PAGE) using 3–6 percent gradient gels. Sixty micrograms (ug) of VLDL protein and 20 ug of chylomicron protein were run on alternate lanes of the gel thereby separating the proteins of each preparation according to size. Visualization of the electrophoretic pattern of protein bands by staining the gel with 0.1 percent Coomassie Blue revealed apo B-100 and apo B-48 bands in chylomicrons and VLDL. The protein bands were then affixed by electrophoretic transfer to nitrocellulose paper to form a solid support. The solid support-affixed apoprotein antigens were then separately immunoreacted with immunopurified MB47 and MB24 receptor molecules. Monoclonal MB47 and monoclonal MB24 receptor molecules immunologically bound to solid phase-affixed antigen were detected using $^{125}$I-labeled goat anti-mouse Ig and autoradiography.

The data so obtained indicated that MB47 and MB24 immunoreact with apo B-100 obtained from LDL, VLDL and chylomicrons, but not with apo B-48 from VLDL or chylomicrons. The ability of both MB47 and MB24 to individually immunoreact with apo B-100 from chylomicrons and VLDL is shown in FIG. 1.

1. Characterization of the Apo B-100 Antigenic Determinant Immunologically Bound By MB47

Previous studies have demonstrated antigenic heterogeneity in apo B-100. That is, some apo B-100 epitopes are not expressed by all LDL particles. Thus, admixture with an excess of certain monoclonal antibodies in a fluid phase RIA does not result in immunological binding of all radiolabeled LDL ($^{125}$I-LDL) particles.

To determine whether the epitope recognized by MB47 receptor molecules was uniformly expressed by all LDL, the ability of MB47 to immunologically bind to $^{125}$I-LDL in a fluid phase RIA was studied. LDL isolated from pooled plasma of 10 normal subjects and from a single normal subject were radiolabeled as described hereinbelow and were admixed with biologically active MB47 receptor molecules to form an immunoreaction admixture. The admixture was maintained under biological assay conditions for a predetermined time period sufficient for the MB47 receptor molecules to immunologically bind to apo B in each sample and form an immunoreaction product (immunoreactant).

Figure 2:
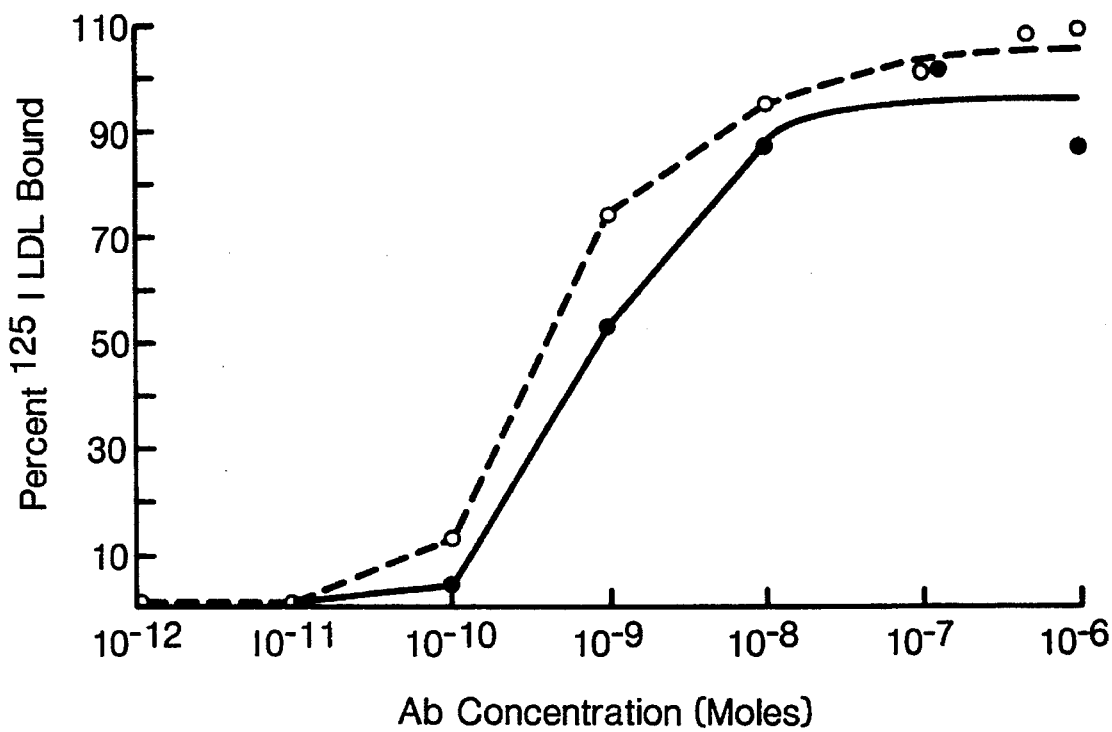
FIG. 2 is a graph showing the percentage of $^{125}$I-labeled LDL particles bound (oridinate) by increasing molar concentrations of monoclonal antibody MB47 [abscissa; Ab concentration (MoAb)] in a fluid phase radioimmunoassay (RIA).

The maximal amount of $^{125}$I-LDL bound by an excess of MB47 receptor molecules was assayed by precipitation of all receptor molecules with IgSORB (The Enzyme Co., Boston, Mass.) and quantitation of $^{125}$I-LDL associated counts in the precipitate in a gamma counter. The results, expressed as a percentage of $^{125}$I-LDL precipitated by trichloroacetic acid (TCA) and shown in FIG. 2, demonstrate that essentially all $^{125}$I-LDL was bound by antibody, indicating that the epitope recognized and bound by MB47 is expressed by all LDL particles.

2. Competitive Inhibition of the Binding of Apo B-100 to LDL-Receptor by MB47

Apoprotein B-100 is the major apoprotein in human and other mammalian LDL, and it mediates binding of LDL to the fibroblast LDL receptor. Previous studies have delineated the central role of the LDL receptor in mammalian lipoprotein metabolism. The fact that LDL particles isolated from multiple animal species bind specifically to the human LDL receptor-binding domain, the binding site on the apo B-100 molecule must be evolutionarily conserved and thus expressed by LDL particles from all animal species.

To examine whether MB47 receptor molecules immunoreact with an antigenic determinant located within the LDL receptor binding domain of human apo B-100, the ability of MB47 to inhibit binding of $^{125}$I-LDL to the cellular LDL receptor was examined. This was accomplished by admixing MB47 receptor molecules, in the form of whole antibody molecules, with $^{125}$I-LDL to form an immunoreaction admixture. The immunoreaction admixture was then maintained under biological assay conditions for a predetermined time period sufficient for the MB47 receptor molecules to immunogically bind the $^{125}$I-LDL present and form an immunoreactant.

Subsequently, the immunoreactant-containing immunoreaction admixture was layered over human fibroblasts that express fibroblast LDL receptors. The cultures were then maintained for a predetermined time period sufficient for the fibroblast LDL receptors to specifically bind any LDL receptor-binding sites available on the $^{125}$I-LDL-MB47 immunoreaction product. It is presumed that such cellular receptor-LDL interaction is inhibitied if receptor molecules as exemplified by MB47 immunoreact with an apo B-100 antigenic determinant whose structure is also involved in LDL-receptor binding.

The results of this study, shown in FIG. 3, indicate that MB47 receptor molecules inhibited cellular receptor-mediated binding, internalization, and degradation of human $^{125}$I-LDL by human fibroblasts to an extent comparable to that produced by a 200-fold excess of unlabeled LDL.

To examine the possibility that MB47 receptors bind to an epitope adjacent to the apo B receptor domain, and because of their size, sterically hinder the binding of apo B to the LDL receptor, the capacity of Fab fragments of MB47 antibody molecules to inhibit human LDL uptake and degradation was also studied in the above described fibroblast assay.

As shown in FIG. 4, MB47-Fab fragments significantly blocked specific cellular binding and degradation of LDL. Because MB47 Fab fragments are substantially smaller than intact MB47-antibody molecules it is believed that the epitope recognized by the MB47 antibody combining site is contained within the LDL receptor binding domain on LDL apo B-100. Antibody MB24 does not have the properties of antibody MB47 and does not inhibit the binding and degradation of $^{125}$I-LDL by cultured fibroblasts.

3. Steric Inhibition

For some embodiments of the assay method of this invention the first and second receptors must bind to different epitopes of the apo B-100 molecule, and those epitopes must be sufficiently separated such that the binding of one receptor does not sterically inhibit the binding of the other receptor. The ability of MB47 and MB24 to competitively inhibit the immunological binding of each other to solid phase-affixed reagent apo B-100 was therefore examined.

The results of that study, shown in FIG. 5, indicate that a 70 fold excess of unlabeled MB24 did not significantly inhibit peroxidase-labeled MB47 from binding to reagent apo B-100. Similarly, a 70-fold excess of unlabeled MB47 did not significantly inhibit peroxidase-labeled MB24 from binding to reagent apo B-100. Thus, MB24 and MB47 bind to different epitopes on apo B-100 and those epitopes are sufficiently separated such that MB24 and MB47 as intact antibodies do not inhibit the binding of each other to a single apo B-100 molecule.

4. Stoichiometry and Affinity of MB47 Binding to Apo B-100

To determine the number of antigenic determinant sites per apo B-100 molecule on LDL that were recognized by MB47 receptor molecules, an antibody-labeled RIA was used. In this assay, MB47 receptor molecules were purified (isolated) from ascites fluid, and were radiolabeled ($^{125}$I-MB47) by well known methods that are described in more detail in the Methods and Materials section.

As shown in FIG. 6A, increasing amounts of $^{125}$I-MB47 were admixed with a fixed amount of apo B-100 in the form of LDL in separate reaction admixtures. The admixtures were maintained under biological assay conditions for a predetermined time period sufficient for the $^{125}$I-MB47 receptor molecules to immunologically bind to the apo B-100 (LDL) and form an immunoreactant. The presence of immunoreactant was then assayed by quantitatively precipitating the LDL (bound and free) using a rabbit antiserum specific for human LDL, and detecting the amount of $^{125}$I-MB47 present as immunoreactant by gamma counting.

The specific immunological binding of $^{125}$I-MB47 receptor molecules was saturable as shown in FIG. 6A. Furthermore, a Scatchard plot of the binding data obtained in these studies was linear (FIG. 6B), suggesting uniformity of MB47 binding sites on LDL particles.

In addition, the apparent affinity constant (Ka) of MB47 for human apo B-100 in the form of LDL as assessed by the antibody-labeled RIA was found to be $3.82 \times 10^9 M^{-1}$. Scatchard analysis also revealed that a maximum of 212 fmoles of $^{125}$I-MB47 antibody bound to 182 fmoles of LDL, indicating that only one MB47 molecule binds to each molecule of apo B-100. That is, MB47 binds to a single, unique antigenic determinant on apo B-100.

The average affinity constant of MB47 for apo B-100 was also assessed in the beforedescribed antigen-labeled RIA. In this competitive equilibrium fluid phase RIA, unlabeled apo B-100 present as LDL produced full displacement of $^{125}$I-LDL. The calculated affinity constant of MB47 receptor molecules present as whole, intact antibody for LDL in this assay was $4 \times 10^9 M^{-1}$, which was in good agreement with the Ka determined by the antibody-labeled assay described hereinbefore.

C. Assay Methods

The receptor molecules of the present invention are particularly useful for assaying the presence and amount of apoprotein B-100 in a body fluid sample such as blood, serum or plasma.

In one embodiment, the present invention contemplates a method for assaying a body sample for the amount of apoprotein B-100 comprising the following steps:

(a) Providing a body sample to be assayed. Typically such a sample is provided as a measured quantity or known amount of blood and more preferably as plasma or serum. Methods for providing samples of blood, plasma and serum are well known in the art and will not be discussed further herein.

(b) Providing receptor molecules in biologically active form that (i) immunoreact with apoprotein B-100 and (ii) are secreted by either the hybridoma having the ATCC accession number HB 8746 or the hybridoma having the ATCC accession number HB 8742, and present in an amount effective for carrying out the assay.

In preferred embodiments the receptor is an intact antibody or a Fab fragment.

The effective amount of receptor molecules can differ, inter alia, with the particular assay method utilized as is well known. Also well known is the ease with which the effective amount can be determined using standard laboratory techniques by one skilled in the art.

(c) Admixing the body fluid sample with the receptor molecules of step (b) to form an immunoreaction admixture.

(d) The admixture is maintained under biological assay conditions for a predetermined time period from minutes to hours such as about 10 minutes to biological assay conditions for a predetermined time about 16–20 hours that is sufficient for the antibody combining sites of the receptor molecules to immunologically bind apoprotein B-100 in the body sample and form an immunoreactant (first complex). Biological assay conditions are those that maintain the biological activity of the receptor molecules of this invention and include a temperature range of about 4 degrees C. to about 45 degrees C., a pH value range of about 5 to about 9 and an ionic strength varing from that of distilled water to that of about one molar sodium chloride. Methods for optimizing such conditions are well known in the art.

(e) Assaying the amount of any immunoreactant that formed and thereby the amount of apo B-100 present in said sample.

In preferred embodiments, the body fluid sample of step (a) is further prepared for assaying according to step (e) by the following steps:

(f) Providing biologically active second receptor molecules secreted by the remaining of either hybridoma of step (b);

(g) Admixing a predetermined amount of the second receptor molecules with the body fluid sample to form an immunoreaction admixture.

(h) Maintaining the second receptor/body fluid sample admixture so formed in a manner similar to that described in step (d) to form a sandwich immunoreactant (second complex) that contains one MB47 molecule and one MB24 molecule immunologically bound to one apo B-100 molecule.

The above described general assay methods can be performed, as is well known in the art, using a variety of different formats. Thus, whereas the more specific assay methods described hereinbelow use solid phase formats, the invention is not so limited.

Solid phase assay formats can be performed using either receptor molecules or antigen affixed to a solid matrix to form a solid support. In those embodiments wherein the solid support contains the receptor of step (b), the admixture of step (c) is a solid/liquid phase admixture and the immunoreactant of step (d) is a solid phase immunoreactant containing body sample apo B-100.

In those embodiments wherein the solid support contains reagent apo B-100, the admixture of step (c) is also a solid/liquid admixture but the body sample apo B-100-containing immunoreactant of step (d) is a liquid phase immunoreactant. Reagent apo B-100 is biologically active; i.e., antigenic, apo B-100 that is provided by a source other than that which is under investigation, typically in the form of isolated LDL.

Assaying the amount of apo B-100 bound as immunoreactant in step (d) can be accomplished, directly or indirectly, by assay techniques well known in the art. For example, homogeneous assay systems such as those described in U.S. Pat. Nos. 4,536,479; 4,233,401; 4,233,402 and No. 3,996,345 which are all incorporated herein by reference, may be used.

In preferred solid phase embodiments, the body fluid is further prepared for assaying by using a labeled specific binding agent. The type and specificity of the labeled specific binding agent depends, as is well known in the art, on the method and format used.

In the preferred solid phase embodiments wherein the solid support contains a receptor of step (b); i.e., a receptor of this invention, the amount of solid phase-bound apo B-100 is prepared for assaying by the following steps:

(i) Providing biologically active labeled second receptor molecules that bind to apoprotein B-100 present in the body sample to form an immunoreactant. The label of the labeled second receptor is capable of signaling the presence of the labeled second receptor in an immunoreactant.

In particularly preferred embodiments, the labeled second receptor molecules immunoreact with a second apo B-100 epitope that is different from the epitope with which the solid phase receptor molecules react and do not substantially inhibit the solid phase receptor molecules from reacting with apo B-100. Preferably, the labeled second receptor molecules are those secreted by the remaining of either hybridoma of step (b); i.e., the recited receptor molecules not chosen as first receptor molecules.

Methods for determining whether a receptor molecule will inhibit (interfere with) the immunological binding to the same antigen of another receptor molecule are well known in the art and are described in more detail hereinbelow.

(j) Admixing a predetermined amount of the labeled second receptor molecules with the body fluid sample to form an immunoreaction admixture.

The admixture so formed can be a liquid admixture as when, step (i) is performed prior to step (b) hereinbefore, or it can be a solid/liquid admixture when the labeled second receptor is admixed substantially simultaneously with or after step (b). When step (i) is performed before or substantially simultaneously with step (b), the labeled second receptor molecules immunoreact with a second apo B-100 epitope that is different from the epitope with which the solid phase receptor molecules react and do not substantially inhibit the solid phase-bound receptor molecules from immunoreacting with apo B-100.

In preferred embodiments step (i) is performed substantially simultaneously with step (b) or after step (c).

(k) The labeled second receptor/body fluid sample admixture so formed is maintained in a manner similar to that described in step (d) to form an immunoreactant.

The solid phase-bound receptor molecules and second receptor molecules are thus immunologically bound to apo B-100 present in the body fluid sample thereby forming a solid phase-bound sandwich immunoreactant that contains label bound as part thereof. That is, a solid phase sandwich immunoreactant that contains a label is formed when one molecule of apo B-100 immunoreacts with both a solid phase-bound receptor molecule and a labeled second receptor molecule. In preferred embodiments, any labeled second receptor molecules that do not form a part of the solid phase-bound immunoreactant (i.e., those not immunologically bound to apo B-100 which itself is bound to solid phase receptor molecules) are separated from the immunoreactant, preferably by washing, prior to assaying for the amount of labeled second receptor present as immunoreactant.

Assaying the amount of immunoreactant formed according to step (e) is accomplished by assaying for the amount of the labeled second receptor bound as part of the immunoreactant that contains apo B-100. This provides a direct assay for the amount of apo B-100 in the sample. That amount can be zero, thereby indicating no apo B-100 present in the sample, within the limits that can be detected. Methods for assaying for the amount of a labeled second receptor depend on the label used, such labels and assay methods being well known in the art.

In the preferred solid phase embodiments wherein the solid support contains reagent apo B-100, the amount of immunoreactant formed in step (d) is prepared for assaying by the following steps:

(l) Admixing a biologically active labeled specific binding agent, preferably a receptor molecule, that binds to any receptor molecules utilized in step (b) present as solid phase immunoreactant to form a complex, preferably a second immunoreactant. The label of the labeled specific binding agent is capable of signaling the presence of the labeled specific binding agent in a complex. In preferred embodiments of these assay types, steps (i)–(k) are carried out after step (d).

(m) Admixing a predetermined amount of the labeled specific binding agent with the body fluid sample to form a reaction, preferably immunoreaction, admixture.

(n) The labeled specific binding agent/first immunoreactant admixture so formed is maintained in a manner similar to that described in step (d) to form a complex.

The solid phase complex thus formed contains a label bound as part thereof. In preferred embodiments, any labeled specific binding agent not bound as part of the solid phase complex is separated from the complex, preferably by washing, prior to assaying for the presence of solid phase-bound label.

Assaying the amount of immunoreactant formed according to step (e) is accomplished by assaying for the amount of label present as part of the complex. This provides an indirect assay for the amount of apo B-100 present in the sample.

The labeling of proteinaceous antigens and specific binding agents is well known in the art. For instance, receptors produced by hybridomas can be labeled by metabolic incorporation of radioisotope-containing amino acids provided as a component in the tissue culture medium. See for example Galfr`e et al., *Meth. Enzymol.* 73, 3–46 (1981).

The techniques of protein conjugation or coupling through activated functional groups are particularly applicable and result in label being covalently linked to antigen or specific binding agent. See, for example, Aurameas, et al., *Scand. J. Immunol. Vol.* 8, *Suppl* 7, 7–23 (1978) and U.S. Pat. No. 4,493,795 which is incorporated herein by reference. In addition, site-directed coupling reaction can be carried out so that the label does not substantially interfere with the biological activity of an antigen or receptor, for example, Rodwell et al., *Biotech.* 3, 889–894 (1985).

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamin-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis" in *Antibody As A Tool,* Marchalonis et al., eds. J. Wiley & Sons, ltd., p. 189–231, 1982, which is incorporated herein by reference.

In preferred embodiments, the indicating group is an enzyme such as horseradish peroxidase (HRPO), glucose oxidase or the like. Where the principal indicating group is an enzyme such as HRPO or glucose oxidase, additional reagents are required to visualize the fact that a receptor-ligand complex (immunoreactant) has formed. Such additional reagents for HRPO include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein.

An exemplary radiolabeling agent is a radioactive element that produces gamma ray emissions. Elements which themselves emit gamma rays, such as $^{124}I$, $^{125}I$, $^{128}I$, $^{131}I$, $^{132}I$, and $^{51}Cr$ represent one class of gamma ray emission-producing radioactive element indicating groups. Particularly preferred is $^{125}I$. Another group of useful indicating groups are those elements such $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium.

The assay methods and systems of the present invention can thus utilize or be comprised of a receptor of this invention affixed to solid matrix to form a solid support.

The antigen or receptor is typically affixed to the solid matrix by adsorption from an aqueous medium although several modes of adsorption, as well as other modes of affixation, well known to those skilled in the art can be used. Exemplary of such modes are the reaction of the receptor or antigen with the reactive carboxyl functionality produced by the reaction of cyanogen bromide with glucose-containing matrices such as cross-linked dextrose or cellulose, gluteraldehyde a linking as discussed hereinafter in conjunction with latex particles and the like.

Useful solid matrices are well known in the art. Such materials include the cross-linked dextran available under the trademark Sephadex from Pharmacia Fine Chemicals (Piscataway, N.J.); agarose; polystyrene beads about 1 u to about 5 mm in diameter (available from Abbott Laboratories of North Chicago, Ill.); polyvinyl chloride, polystyrene, cross-linked polyacrylamide, nitrocellulose or nylon-based webs such as sheets, strips or paddles; or tubes, plates or the wells of a microtiter plate such as those made from polystyrene or polyvinylchloride.

Latex particles useful in agglutination-type assays are also useful solid matrices. Such materials are supplied by the Japan Synthetic Rubber Company of Tokyo, Japan, and are described as carboxy-functional particles dispersed in an anionic soap. Typical lots of such particles have an average diameter of 0.308 microns (u), and have an average carboxy-functional group distribution of about 15 to about 30 square Angstroms per carboxy group.

Prior to use, the particles are reacted with a diamine such as 1,3-diamino-2-propanol to form a plurality of amide bonds with the particle carboxy groups while maintaining free amine groups. The free amines are thereafter reacted with a dialdehyde such as glutaraldehyde and the receptor or antigen to form Schiff base reaction products. The Schiff base reaction products are thereafter reduced with a water-soluble reductant such as sodium borohydride to provide a useful solid support.

Those skilled in the art will understand that there are numerous methods of solid phase immunoassays that may be utilized herein. Exemplary, useful solid phase assays include enzyme multiplied immunoassay techniques (EMIT) and fluorescence immune assays (FIA), in addition to the specifically discussed RIAs and ELISAs. However, any method that results in a detectable reaction of apoprotein B-100 with receptor molecules of this invention is considered part of this invention. Each of those assay methods can employ single or double antibody techniques in which an indicating means is utilized to signal the immunoreaction, and thereby the binding of any apoprotein B-100 that is to be assayed with a receptor of this invention. Exemplary techniques can be found explained in Maggio, *Enzyme Immunoassay*, CRC Press, Cleveland, Ohio (1981); and in Goldman, *Fluorescent Antibody Methods*, Academic Press, New York, N.Y. (1980).

One embodiment of a specific method for assaying a body fluid sample for apo B-100 using a solid phase-affixed receptor of this invention is a noncompetitive ELISA wherein the immunoreactions are performed sequentially. In such an assay an aliquot of MB47 receptors, e.g., generally about 1 to about 500 ug, is affixed to the inner walls of a microtiter well to form a solid support.

Any apo B-100 present in the body sample provided is then immunoreacted with the solid phase-affixed receptors. This is accomplished by admixing a known amount, e.g., about 10 to about 200 microliters (ml) of sample (that can be prediluted) such as serum of plasma in the microtiter well with the solid phase-affixed receptors to form a solid/liquid phase admixture. The admixture is maintained under biological assay conditions for a predetermined time period sufficient for any apo B-100 present in the sample to immunologically bind to the receptor molecules and form a solid phase immunoreactant. The solid and liquid phases are thereafter separated, and the solid phase is typically rinsed to help assure removal of nonspecifically bound materials.

Apo B-100 present as solid phase immunoreactant (i.e., apo B-100 bound to solid phase-affixed MB47 receptors) is then immunoreacted with enzyme-labeled second receptor molecules. This is accomplished by admixing a predetermined amount, e.g., about 0.1 to about 10 ug of enzyme-labeled second receptor molecules in aqueous buffer solution, preferably horseradish peroxidase (HRPO)-labeled MB24 receptors, to form a second solid/liquid admixture. The second admixture is maintained as described hereinabove, thus forming a solid phase immunoreactant "sandwich" consisting of MB47 receptor, apo B-100 and enzyme labeled MB24 receptors.

After separating the liquid phase from the solid phase as previously described, an aliquot of chromogenic substrate, such as o-phenylenediamine (OPD) for HRPO is admixed in the microtiter well containing the solid phase immunoreactant to form a third solid/liquid admixture. This admixture is maintained under biological assay conditions for a predetermined time period sufficient for any enzyme present as immunoreactant to convert a proportional amount of substrate into a colored product. The optical density of the resulting colored solution is then measured and compared to results obtained using solutions containing known amounts of reagent apo B-100.

The ability of the noncompetitive sequential ELISA described above and in more detail in the Materials and Methods section to detect apo B-100 in a body fluid sample was examined. In those studies, aliquots of lipoprotein depleted human plasma (LDP) to which were admixed known amounts of reagent apo B-100 served as control body fluid samples.

The results of that study, shown in Table 1 below demonstrate that the above-described method can accurately assay clinically relevant amounts of apo B-100 present in a body fluid sample.

TABLE 1

Noncompetitive Sequential ELISA Studies of Apo B-100 In Human Plasma

| Sample[1] | Actual[2] | Ref[3] | MB47/MB24[4] | MB24/B18[5] |
|---|---|---|---|---|
| B Low | 40 | 32 ± 44.3 | 42.6 ± 5.0 | 31.7 |
| B Normal | 80 | 71 ± 103 | 82.3 ± 11.8 | 54.7 |
| B High | 150 | 126 ± 180 | 149 ± 24.7 | 119 |
| T Urn | 22.3 | 12.6 ± 17 | 16.2 ± 0.62 | 15.4;9.0 |
| T Normal | 44.8 | 25.4 ± 49.2 | 36.1 ± 9.4 | 22.9;19.7 |
| T High | 89.5 | 64.0 ± 101 | 77.4 ± 7.4 | 34.9;36.3 |
| A | | 73 | 82.9 ± 11.7 | 66.4 |
| AM | | 76 | 67.1 ± 8.1 | 46.8;61.0 |
| B | | 86.5 | 69.8 ± 4.6 | 68.5;90.5 |
| C | | 145 | 129 ± 3.8 | 147.173 |
| D | | 109 | 81.0 ± 7.4 | 76.3;98.2 |
| K | | 95 | 98.4 ± 16.5 | 77.5;88.9 |
| R | | 60 | 64.2 ± 7.5 | 51.3;52.9 |
| Pool | | 81.3 | 78.5 ± 6.8 | 54.7;65.9 |
| C1 | | 40.1 | 47.9 ± 6.7 | 47.0;68.7 |
| C2 | | 74.8 | 88.6 ± 13.2 | 81.3;98.2 |
| C3 | | 70.4 | 64.5 ± 4.8 | 64.5;82.9 |
| C4 | | 39.9 | 56.7 ± 6.6 | 48.5;58.0 |

[1]Clinically low, normal and high apoprotein B-100-containing control solutions were obtained from Johnson & Johnson Biotechnology Center, Inc., La Jolla, CA (B) and Tago, Inc., Burlingame, CA (T). Plasma samples were obtained from clinically normal individuals (one or two letter designations and C1–C4), and the pool represents an admixture of 10 such samples.
[2]Actual apoprotein B-100 concentration as determined by total protein added to the sample. All concentrations shown in the Table are in units of mg/dl.
[3]The concentration of apoprotein B-100 as determined using the reference assay (Ref.) described hereinafter. Values are given as a three standard deviation range.
[4]Apoprotein B-100 concentrations (mean ± 3 standard deviations) obtained using solid phase-affixed MB47 receptors and HRPO-labeled MB24 receptors in the noncompetitive sequential ELISA as described hereinbefore.
[5]Apoprotein B-100 concentrations (replicate values shown where performed) obtained using solid phase affixed MB24 receptors and HRPO-labeled B18 receptors (Curtiss et al., J. Biol. Chem., 257, 15213–15221 (1982)) in the noncompetitive ELISA wherein the immunoreactions were performed sequentially with the solid phase immunoreactant being formed first.

Another embodiment of a specific method for assaying a body fluid sample for apo B-100 is a noncompetitive ELISA wherein the immunoreactions are performed substantially simultaneously. To the before-described microtiter well containing solid phase affixed MB47 receptors is admixed substantially simultaneously the provided body sample and enzyme-labeled second receptors that immunoreact with a second apo B-100 epitope and do not substantially inhibit the binding of MB47 receptors to apo B-100. Such enzyme labeled second receptors are preferably MB24 receptors.

The resulting solid/liquid admixture is then maintained, separated and the amount of enzyme present as part of the solid phase bound immunoreactant sandwich determined as previously described.

The above described noncompetitive ELISA was used to examine the apo B-100 content of plasmas from 20 patients with coronary artery disease (CAD), 20 patients with familial hypercholesterolemia and 20 normal subjects. As shown in Table 2 below, the mean plasma apo B-100 level of the normal subjects was determined to be 85 milligrams/deciliter (mg/dl) with a 2 standard deviation range of ±21 mg/dl. This value is in close agreement with the normal range of apo B values reported by Curry et al., *Clin. Chem.* 24, 280–286 (1987), and Rosseneu et al., *Clin. Chem.* 28, 427–433 (1983) each using different immunoassays.

Furthermore, the plasma apo B-100 levels in patients with CAD and hypercholesterolemia were higher than the upper limit of the 2 standard deviation range found for normals. Similar results using other techniques for CAD and hypercholesterolemia patients have been reported by Sniderman et al., *Proc. Natl. Acad. Sci. USA* 77, 604–608 (1980) and Lipid Research Council, *JAMA* 251, 351–364 (1984).

TABLE 2

Simultaneous ELISA Studies of Apo B-100 In Human Plasma

| | Lipoprotein Levels[2] | | | | Apoprotein B Levels[3] | | |
|---|---|---|---|---|---|---|---|
| Subjects[1] | Total[3] Chol. | HDL[4] Chol. | LDL[5] Chol. | Compet.[6] ELISA | Non-Compet.[7] ELISA | RID[8] #1 | RID[9] #2 |
| Normal | 186 | 60 | 111 | 85 | 82 | 102 | 69 |
| ±SD | 37 | 16 | 30 | 21 | 22 | 20 | 19 |
| CAD | 205 | 37 | 133 | 109 | 104 | 138 | 84 |
| ±SD | 35 | 7 | 37 | 24 | 23 | 20 | 24 |
| FH | 331 | 37 | 270 | 196 | 204 | 211 | 136 |
| ±SD | 90 | 11 | 96 | 40 | 49 | 64 | 44 |

[1]Subjects include 20 normolipidemic, healthy controls (normal); 20 subjects with coronary artery disease defined by cardiac catheterization (CAD); and 20 subjects with familial hypercholesterolemia (FH).
[2]Values given are mean ± 2 standard deviations from mean (±SD) in units of mg/dl.
[3]Total cholesterol.
[4]Cholesterol present as HDL.
[5]Cholesterol present as LDL.
[6]Apo B-100 level as determined by the competitive (Compet.) ELISA described in the Materials and Methods section.
[7]Apo B-100 level as determined by noncompetitive (Non-Compet.) ELISA using solid phase affixed MB47 receptors and HRPO-labeled MB24 receptors wherein the sample and receptors were substantially simultaneously admixed.
[8]Apo B level determined using the radial immunodiffusion kit model Diffu-gen RID available from Tago, Inc., Burlingame, CA
[9]Apo B level determined using the radial immunodiffusion kit model M-Partigen RIA available from Calbiochem-Behring, La Jolla, CA The effect of diluting the body fluid sample prior to assaying it for apo B-100 by a noncompetitive simultaneous ELISA method was also examined. Those results, shown in Table 3 below, indicate there was no significant difference in the apo B-100 levels determined over a 5 fold range of plasma dilutions, i.e., 1:1000 to 1:5000.

TABLE 3

Simultaneous ELISA Studies of Apo B Levels Determined from Different Dilutions of Plasma

| Plasma Dilution | Plasma 1[1] | Plasma 2[1] | Plasma 3[1] |
|---|---|---|---|
| 1:1000 | 54.4 | 136.6 | 199.0 |
| 1:2500 | 57.5 | 142.5 | 194.2 |
| 1:5000 | 53.0 | 126.0 | 178.0 |
| Mean[2] | 55.0 | 135.0 | 190.0 |
| S.D.[3] | 1.88 | 6.83 | 8.98 |
| % C.V.[4] | 3.4 | 5.0 | 4.7 |

[1]Plasma apo B-100 concentration in units of mg/dl.
[2]Mean plasma apo B-100 concentration for all 3 dilutions.
[3]One standard deviation.
[4]Percent coefficient of variance between results obtained for the various dilutions.

Correlation between LDL cholesterol and plasma apo B-100 levels as determined by a noncompetitive ELISA for the normal and patient samples described above is shown in FIG. 7. The correlation coefficient of 0.89 is similar to that reported by Albers et al., *Metabolism* 24, 1339–1351 (1975) and Slater et al., *Clin. Chem.* 31, 841–845 (1985).

Embodiments of the assay methods of this invention using a solid support containing reagent apo B-100 affixed to a solid matrix affixed to a solid matrix are performed using the following steps:

(a) A body fluid sample containing apo B-100 is provided as described hereinbefore.

(b) Substantially simultaneously admixing (1) the fluid sample;

(2) a predetermined amount of either MB24 or MB47 receptor molecules; and (3) a predetermined amount of solid phase-affixed reagent apo B-100, to form a liquid/solid phase immunoreaction admixture.

The admixture is maintained under biological assay conditions for a time period sufficient for the antibody combining sites of the receptor molecules to immunoreact with (immunologically bind to) either the reagent apo B-100 or any apo B-100 present in the body fluid sample. The receptor molecules immunologically binding apo B-100 present in the body sample form a liquid phase immunoreactant and those binding solid phase-affixed reagent apo B-100 form a solid phase immunoreactant.

(c) The presence of the solid phase-affixed immunoreactant is then assayed and the amount of apo B-100 present in the sample is thereby determined by comparison of the amount of binding exhibited by a known amount of MB47 or MB24 admixed with similar solid phase-affixed apo B-100, as discussed hereinafter. Preferably, the immunoreactant assay is performed after the liquid phase and solid phase immunoreactant of step (b) are separated, as by washing. The amount of sample apo B-100 bound as liquid phase immunoreactant can be determined as by the use of labeled antibodies that immunoreact with the receptor molecules of this invention such as peroxidase-linked goat anti-mouse Ig, or as otherwise described herein.

In a particularly preferred embodiment of the competition assay, about 1 ug to about 10 ug of reagent apo B-100 are affixed to a solid matrix, preferably the walls of a microtiter well, to form a solid support. Any nonspecific binding sites on the solid support are typically blocked with a protein such as BSA or the like.

A predetermined amount of receptor molecules of this invention, e.g., generally about 0.1 ug to about 10 ug, is substantially simultaneously immunoreacted with the solid phase-affixed reagent apo B-100 and any apo B-100 present in a body fluid sample (which can be diluted) such as serum or plasma. This is accomplished by substantially simultaneously admixing an aliquot of sample and the receptor molecules in the microtiter well containing solid phase-affixed reagent apo B-100.

The solid/liquid admixture thus formed is maintained under biological assay conditions for a time period sufficient for the receptor molecules present to immunologically bind the apo B-100 present. The solid and liquid phases are preferably thereafter separated as by washing and the solid phase is typically rinsed to help assure removal of non-specifically bound materials.

The presence of solid phase-affixed immunoreactants is then assayed typically by use of labeled antibodies that immunologically bind the receptor molecules of this invention such as peroxidase-labeled goat anti-mouse IgG.

In the competitive ELISA, apo B-100 present in the patient sample competes with a constant, known amount of reagent apo B-100 for a constant, known number of receptor molecule antibody combining sites in the immunoreaction admixture. Competition provided by the sample apo B-100 results in a decrease of detectable solid phase-affixed immunoreactant; the greater the decrease, the greater the amount of apo B-100 present in the body sample under investigation.

To obtain relative amounts of apo B-100 present in patient plasmas, results obtained using apo B-100 present in patient plasma as competitors were compared to results obtained using competitive standards containing known amounts of reagent apo B-100. A standard curve was prepared using LDL concentrations ranging from 32 mg/ml to 0.25 mg/ml (320 mg/dl to 2.5 mg/dl).

The competitive ELISA described above was used to examine the same normal and patient samples evaluated by noncompetitive ELISA. Those results, also shown in Table 2 hereinbefore, are in close agreement with the results obtained by the noncompetitive assay.

The effect of diluting the body fluid sample prior to assaying it for apo B in the above-described competitive ELISA was examined. Those results, shown in Table 4 below, demonstrate no significant difference in the apo B levels determined over a 4-fold range of plasma dilutions;. i.e., 1:100 to 1:400.

TABLE 4

Competitive ELISA Studies of Apo B Levels Determined From Different Plasma Dilutions

| Plasma Dilution | Plasma 1[1] | Plasma 2[1] | Plasma 3[1] |
|---|---|---|---|
| 1:100 | 32.8 | 63.3 | 175.8 |
| 1:200 | 30.0 | 58.5 | 183.2 |
| 1:300 | 31.8 | 64.8 | 190.9 |
| 1:400 | 33.8 | 62.6 | 190.0 |
| Mean[2] | 32.1 | 62.3 | 185.0 |
| S.D.[3] | 1.6 | 2.7 | 7.0 |
| % C.V.[4] | 5.0 | 4.3 | 3.8 |

[1]Plasma apo B-100 concentration in units of mg/dl.
[2]Mean plasma apo B-100 concentration for all 3 dilutions.
[3]One standard deviation
[4]Percent coefficient of variance between results obtained for the various dilutions.

Correlation between LDL cholesterol and plasma apo B levels as determined by the competitive ELISA for the normal and patient samples described above is shown in FIG. 8. The correlation coefficient of 0.92 is similar to that reported by Albers et al., *Metabolism*, 24, 1339–1351 (1975), and Slater et al., *Clin. Chem.*, 31, 841–845 (1985), thus indicating that the competitive ELISA accurately predicts circulating LDL cholesterol levels.

The correlation between apo B-100 levels obtained using the competitive and noncompetitive ELISAs was examined. As shown in FIG. 9 there was a high correlation (r=0.92) between the results obtained in each assay.

A diagnostic system, preferably in kit form, useful for carrying out the above assay methods includes, in separate packages, (a) a first specific binding agent wherein said agent is (i) a receptor that immunoreacts with apo B-100, and is selected from the receptor secreted by hybridoma HB 8746 (MB47) or the receptor secreted by hybridoma HB 8742, (MB24) and (b) a labeled second specific binding agent for signaling the immunoreaction of said first binding agent with apo B-100. Preferably, the labeled specific binding agent is a receptor linked to an enzyme. More preferably, the labeled agent is the remaining of either receptor of (a) above, linked to an enzyme.

In preferred embodiments, the system further includes another container of reagent apo B-100 for use as control and/or target antigen. Also preferred are embodiments wherein the system includes a solid matrix to which the first specific binding agent or reagent apo B-100 is affixed to form a solid support. Useful solid matrices are as already described. Preferably, however, the solid matrix is the well of a microtiter plate.

Known amounts of the specific binding agents are provided. Those amounts are at least enough to carry out one assay. The provided specific binding agents are typically supplied in a form and amount that is designed to be diluted to a prescribed volume with water, saline or a buffer such as phosphate-buffered saline at pH 7.3–7.5.

Additional packages can also be included in the system. Such packages can contain (i) buffer salts in dry or liquid form, (ii) enzyme substrates such as o-phenylenediamine, and the like.

Exemplary packages include glass and plastic such as polyethylene and polypropylene bottles or vials; plastic, plastic-metal foil, plastic-metal foil-paper envelopes and the like. The specific binding agents can be packaged in an aqueous liquid form as in ascites or buffer, but preferably, they are supplied in dried form such as that provided by lyophilization.

D. Affinity Sorbants

The present invention also contemplates an affinity sorbant, preferably sterile, comprised of a biologically active receptor of this invention affixed to a solid matrix to form a solid support. The solid matrix is preferably in particulate form. Such affinity sorbents are useful for specific removal of apoprotein B-100 containing lipoprotein (VLDL and LDL) by immunoadsorption from plasma of patients suffering from hypercholesterolemia.

The solid support can be a wide variety of materials such as cross-linked dextran, e.g., Sephadex G-25, -50, -100, -200 and the like available from Pharmacia Fine Chemicals of Piscataway, N.J., agarose and cross-linked agarose, e.g., Sepharose 6B, CL6B, 4B, CL4B and the like also available from Pharmacia Fine Chemicals or Bio-Gel A-0.5M, A-1.5M, A-50M and the like available from Bio-Rad Laboratories, Richmond Calif., or polyacrylamide beads, e.g., Bio-Gel P-2, P-30, P-100, P-300 and the like also available from Bio-Rad Laboratories. The agarose and cross-linked agarose materials are preferred herein because of their high porosity and low non-specific binding properties and will be used illustratively as a solid matrix.

Sterilization of the receptors and solid matrix is typically performed before linking. To maintain biological activity, receptors are usually sterilized by filtration, for example by passage through a 0.22 micron nitrocellulose filter. Sterilization of the matrix depends, as is well known, on the type of matrix. For example, Sepharose cannot be sterilized by autoclaving, but it can be sterilized chemically, for example, by treatment with diethylpyrocarbonate. On the other hand, cross-linked Sepharose can be sterilized by autoclaving at pH 7, 120 degrees C. for 20 minutes.

The Sephadex or Sepharose matrix is typically activated for linking using cyanogen bromide by methods well known in the art. The activated matrix is then washed and linked to receptors that immunoreact with apo B-100 and are secreted by hybridoma HB 8746 or hybridoma HB 8742. The matrix-linked receptor is then washed and is ready for use. Unreacted reactive groups on the support can be reacted with an amine such as ethanolamine or Tris if desired.

The affinity sorbant can be used in its loose state but is preferably confined in a column. Plasma from a patient containing apo B-100 is then admixed with the affinity sorbant to form an immunoreaction admixture. The admixture is maintained under biological assay conditions for a time period sufficient for the solid matrix-affixed receptors to immunologically bind apo B-100 present in the plasma and form a solid matrix-affixed immunoreactant. The plasma is then separated from the solid matrix-affixed immunoreactant. The apo B-100 (LDL and VLDL)-depleted plasma so produced can then be introduced into the patient from which it was originally obtained.

The preparation of an affinity sorbant and its use for removal of apolipoprotein B contained lipoproteins from plasma are described in Stoffel et al., *Proc. Natl. Acad. Sci. USA* 78, 611–615 (1981), which is incorporated herein by reference. An affinity adsorbant column prepared by linking substantially pure MB47 receptors to CNB4-activated Sepharose 4B was found to immunoadsorb (bind) 3mg of LDL per ml of solid support.

II. Materials Methods

A. Preparation of Human Lipoproteins

Human lipoprotein fractions were isolated by centrifugation at the following densities: VLDL, density (d) less than 1.006 gm/ml; LDL, d equal to 1.025–1.050 gm/ml; HDL, d equal to 1.070–1.21 gm/ml, and LDS, d equal to 1.21 gm/l). In some cases, human LDL was also isolated at d 1.019–1.063 gm/ml or at 1.045–1.065 gm/ml. The protein concentration of plasma and each fraction were determined by the Lowry technique [Lowry et al., *J. Biol. Chem.* 193, 265–275, (1951)] as modified by Markwell et al., *Anal. Biochem.* 87, 206–210 (1978), using a BSA standard.

For each LDL and VLDL fraction, estimations of apo B content were also made following precipitation of apo B with tetramethylurea (TMU) using the technique of Kane et al., *J. Clin. Invest.*, 56, 1622–1634, (1975)) or isopropyl alcohol following the teachings of Equsa et al., *J. Lipid Res.*, 24, 1261–1267 (1983).

Fresh, fasting human plasma was obtained from normal healthy donors by plasmaphoresis, and was adjusted to 0.1 percent EDTA (s/v). Pools made up from three or more donors were used unless otherwise stated. The lipoproteins were isolated by sequential ultracentrifugation of the plasma using solid KBr for density (d) adjustment. The lipoprotein fractions included VLDL, d less than 1.006 g/ml; IDL, d=1.006–1.019 g/ml; LDL, d= 1.019–1.063 g/ml; and HDL, d=1.063–1.25 g/ml.

The bottom fraction containing lipoprotein-depleted serum (d greater than 1.25 g/ml) was also collected.

The fractions were dialyzed thoroughly against lipoprotein buffer containing 0.15M NaCl, 0.3 mM EDTA, 0.0005 percent alpha-tocopherol at a pH value of 7.4.

A chylomicron fraction was separated from the VLDL fraction of non-fasting pooled plasma by floating the chylomicrons through lipoprotein buffer with ultracentrifugation at 120,000 xg for 40 minutes at 4 degrees C.

All lipoproteins were filter-sterilized, and stored at 4 degrees for no more than 20 days. Lipoproteins were analyzed for protein content by a modification of the method of Lowry, *J. Biol. Chem.* 193, 265–275 (1951), using a BSA standard. All lipoprotein concentrations are expressed on the basis of protein.

The apoprotein composition of each of the lipoprotein classes was assessed by SDS-polyacrylamide gel electrophoresis. The chylomicrons contained detectable amounts of apoproteins, B, E and C, while the VLDL contained apoproteins B, E, C and trace amounts of apoprotein A–I.

The IDL contained apoproteins, B, E and C, while the LDL contained only apoprotein B. The HDL contained apoproteins AI, AII and C.

During the course of these studies, lipoprotein preparations displayed a consistent apoprotein composition. To control for potential proteolysis of apoproteins, selected plasma pools were isolated and stored in the presence of 1 mg/ml gentamycin sulfate, 0.2 percent sodium azide, and 1 mM benzamidine, 10 mM diisopropyl fluorophosphate, 10 ug/ml soybean trypsin inhibitor.

Comparison of SDS-PAGE apoprotein-staining patterns of these lipoproteins, as well as those isolated in the absence of antibiotics and protease inhibitors immediately after ultracentrifugation and after storage for up to 3 weeks showed no evidence of proteolysis. All preparations that were used were sterile.

B. Hybridoma Production and Culture

Intact native lipoproteins isolated from pooled plasma were used for immunization. Balb/c mice four to five weeks of age were immunized intraperitoneally with 50 micrograms of lipoprotein in complete Freund's adjuvant. Secondary intraveneous injections of 50 ug of lipoprotein in lipoprotein buffer were given between day 28 and 33. Spleens were removed from the immunized mice 72 hours after the last injection and single cell suspensions were prepared in HT medium. Blood was also collected, and the serum was used as a positive control for each of the immunoassays.

The murine myeloma cell lines were maintained in log phase growth in stationary cultures in complete HT medium [Kennet et al. *Curr. Top. Microbiol. Immunol.* 81, 77–91 (1978), which is incorporated herein by reference] containing 0.1 mM azaguanine. Fusions were performed in the presence of 30 percent (v/v) polyethylene glycol 1000 (Sigma, St. Louis, Mo.) at a ratio of immune spleen cells to P3×63Ag8 of 10:1. Three days after fusion, the cells were plated out in 96-well tissue culture plates at 1×10⁵ viable cells/well in HT medium containing 0.1 mM aminopterin.

The cells were fed 7 days after fusion with HT medium and at approximately 4–5 day intervals thereafter as needed. Growth was followed microscopically and culture supernatants were collected on day 14 for assay of antigen-specific antibody production by a solid phase RIA. Specific antibody-producing hybridomas were cloned 19 to 47 days after fusion by limiting dilution in the presence of Balb/c splenic feeder cells, and hybridomas in wells containing single colonies were screened for antibody production by solid phase RIA after 10 days. The cloned hybridomas were cultivated in medium containing 10 percent calf serum, and were stored frozen in liquid nitrogen.

C. Inibition of LDL Binding, Internalization and Degradation

The ability of anti-apo B-100 receptors to inhibit binding, internalization and degradation of $^{125}$I-LDL by human fibroblasts was assessed in the following manner. LDL was iodinated with $^{125}$I (specific activity 200 cpm/ng) using the iodine monochloride technique of Bilheimer et al., *J. Clin. Invest.*, 56, 1420–1430 (1975).

To allow antibody-LDL interaction, 0.1 ml of each hybridoma supernatant was incubated (admixed and maintained) with $^{125}$I-LDL (final concentration 2.5 mg/ml) in 0.4 ml of Dulbecco's minimal essential medium (DME) containing 2.5 mg/ml lipoprotein-deficient serum (LDS) for 12 hours at 4 degrees C. Then, the individually incubated mixtures were transferred to human foreskin fibroblast monolayers grown in DME with 10 percent fetal calf serum (FCS) in 10 millimeter-diameter wells. LDL receptors of these cells had been maximally expressed by prior incubation of those cells for a time period of 24 hours in DME containing 2.5 mg/ml LDS.

After individual incubations of supernatant and fibroblast cells for 6 hours at 37 degrees C., the cellular degradation of $^{125}$I-LDL was assessed in accordance with the method of Drevon et al., *J. Lipid Res.*, 22, 37–46 (1981). Control cultures had 0.4 ml of DME containing $^{125}$I-LDL and one of the following: a) 0.1 ml of fresh hybridoma medium containing 20 percent fetal calf serum; or b) 0.1 ml hybridoma medium from wells of hybridoma colonies that were negative for apo B-specific antibody production; c) 0.1 ml DME containing 2.5 mg/ml LDS; or d) 0.1 ml unlabeled LDL (to bring final unlabeled LDL concentration in the media to 500 ug per ml).

D. Isolation of Anti-LDL Immunoglobin

Ascites fluids containing receptors of this invention were obtained from 10-week-old Balb/c mice, which had been primed with 0.3 ml of mineral oil and injected intraperintoneally with 3–50×10⁵ hybridoma cells. The average time for development of ascites was 12 days. Following clarification by centrifugation at 15,000 xg for 1 hour at 4 degrees C., ascites fluids were pooled and stored frozen at −20 degrees C.

Isolated antibody MB47 was prepared by chromatography of the monoclonal hybridoma ascites fluids on a protein A-Sepharose 4B column (Pharmacia Fine Chemicals, Piscataway, N.J.). Antibody was eluted from the column with 0.1 molar (M) acetic acid.

Isolated receptors also were prepared by fast protein liquid chromatography (FPLC) of a monoclonal hybridoma ascites fluid on a Pharmacia Mono Q HR 5/5 anion exchange column in a Pharmacia FPLC System using a 0–0.5M NaCl gradient in 10 mM Tris, pH 8.0, and following the directions supplied with the column.

E. Characterization of Hybridoma Antibodies

The total gamma-globulin (Ig) content of each pool of ascites fluid was obtained by electrophoresis of 1–3 ml samples of cellulose acetate strips in 75 mM veronal buffer, at a pH value of 8.6 for 45 minutes at 200 millivolts (mV). The percentage of the total protein that was Ig was quantitated by densitometric scanning of the Ponceau S-stained gels, and total protein was determined by the modified Lowry methods as discussed before.

Murine Ig heavy and light chains were identified by double diffusion in 0.9 percent agarose. Ten microliters of an appropriate dilution of ascites fluid were reacted with an equal volume of appropriately diluted rabbit anti-murine heavy and light chain-specific antisera (Litton Bionetics). Following diffusion for about 15 hours at 20 degrees C. and washing, precipitin lines were identified by staining with 0.5 percent Coomassie brilliant blue R-250.

Isoelectric profiles of each monoclonal antibody were obtained by isoelectric focusing of 0.01 ml samples of the ascites fluids in 0.8 percent agarose (EF 802-300 LKB) containing 10 percent sorbitol, 2 percent ampholine within a pH value range of 5–8, (LKB) for 150 minutes at 3 watts constant power. Following fixing and drying, the gels were stained with Coomassie brilliant blue and photographed.

1. Western Blotting—Apoproteins were separated by sodium dodecyl sulfate-polyacrylamide gel electrophoresis (SDS-PAGE) of the lipoproteins in a vertical slab gel apparatus (14×12×0.15 cm) (Hoeffer Scientific Instruments, San Francisco, Calif.). The gels were prepared using a 25 mM Tris-glycine buffer at a pH value of 8.6. The upper stacking gel contained 1 percent SDS, 3 percent acrylamide, and the lower running gel was either a 3 to 20 percent or a 3 to 6 percent acrylamide gradient containing 1 percent SDS. The lipoproteins were delipidated by boiling for 3 minutes in electrophoresis sample buffer that contained 1 percent sodium dodecyl sulfate, 10 mM Tris, and 0.24 mM EDTA. Molecular weight markers and their respective apparent relative molecular masses were: fibrinogen, 340,000; IgG, 140,000; albumin, 69,000; ovalbumin, 43,000; soybean trypsin inhibitor, 20,500; and lysozyme, 14,300. The gels were electrophoresed for approximately 18 hours at 13.5 milliamps (mA) constant current.

The gels were washed in distilled water for 10 minutes and then for 10 minutes in 25 mM Tris, 192 mM glycine, pH 8.3, containing 20 percent (v/v) methanol. Transfer to nitrocellulose (0.45 micro, Millipore Corp.) was accomplished by electrophoresis for 1 hour at 400 mA. Remaining active binding sites on the nitrocellulose were saturated by soaking overnight in PBS containing 3 percent BSA, 3 percent normal goat serum, 0.01 percent sodium azide (blocking solution).

The fixed gels or the nitrocellulose transfers were incubated for 18 hours at 4 degrees C. with either immune mouse serum or ascites fluid appropriately diluted in PBS containing 3 percent BSA, 3 percent normal goat serum, 0.05 percent Tween-20 (polyoxyethylene (20 monolaurate). After repeated washing, antibody binding was detected by a second 4 hour incubation at 4 degrees C. with $^{125}$I-goat anti-immune Ig (0.5 microCi/ml) in the same buffer followed again by extensive washing.

Nonspecific binding to the nitrocellulose was significantly reduced by washing after incubation with both the first and second antibodies in PBS containing 3 percent BSA, 0.05 percent Tween-20 and then in 0.5M LiCl containing 0.1 percent SDS.

The gels or nitrocellulose transfers were dried and analyzed by autoradiography (X-Omat; Eastman Kodak) at −20 degrees C. Where appropriate, gels were stained with either 0.1 percent Coomassie brilliant blue R-250 in 50 percent trichloroacetic acid or silver stain (Bio-Rad) as described by Merril et al., *Proc. Natl. Acad. Sci. USA*, 76, 4335–4339 (1979).

F. Preparation of Fab Fragments

Fab fragments of isolated receptor molecules antibody were formed by digestion with papain. The antibody Fc portions and undigested antibodies were removed by passage over a protein A-Sepharose 4B column. SDS-PAGE of the Fab fragments revealed two discrete bands of 25,000 and 40,000 daltons. Immunoreactivity of the Fab fragments was verified by specific binding to LDL in a solid phase RIA (Milne et al., *Arteriosclerosis* 3, 23–30 (1983)).

G. Radioimmunoassays (RIA)

1. Fluid Phase $^{125}$I-Labeled Antigen RIA

To determine the fraction of $^{125}$I-LDL particles bound by MB47 and MB24, a fluid phase RIA was utilized [Curtiss and Edgington, *J. Biol. Chem.*, 25, 15213–15221 (1982)]. Two different LDL (d=1.019–1.063 gm/ml) preparations were studied, one isolated from pooled plasma of 10 normal subjects and one isolated from plasma of one normal subject. $^{125}$I-LDL (2000 cpm/ng), prepared using the Iodogen (Pierce Chemical Co., Rockford, Ill.) technique, was 90 percent trichloracetic acid (TCA) precipitable. It was diluted in 9 percent bovine serum albumin (BSA) (Sigma, St. Louis, Mo.) and centrifuged at 30,000 xg for 15 minutes prior to each assay to remove complex material. Assays were performed in 12×75 mm glass tubes in triplicate in 55 mM sodium barbital buffer, at a pH value of 8, containing 150 mM NaCl, 0.02 percent sodium azide, 3 percent BSA, and 1.5 mM sodium-EDTA. To 0.1 ml of $^{125}$I-LDL (containing 20 ng LDL protein) were added 0.1 ml of buffer or competing antigen and 0.1 ml of increasing concentrations of isolated MB47 receptors diluted in the BSA-barbital buffer. After 18 hours at 4 degrees, 0.1 ml of IgSorb (The Enzyme Co., Boston, Mass.) were admixed. After 2-hours of maintenance time, 2 ml of BSA-free barbital buffer were added, and the tubes were immediately centrifuged at 1,500 xg for 60 minutes. The precipitates were washed twice with barbital buffer. Maximum precipitable radioactivity was determined by replacing the IgSORB with 100 percent TCA. The minimum precipitable radioactivity was determined in the absence of MB47 receptors. The percent $^{125}$I-LDL bound was then calculated.

2. Fluid Phase $^{125}$I-labeled Receptor RIA

Intact antibody MB47 receptors, isolated by immunopurification, were iodinated with $^{125}$I using the Iodogen technique (specific activity 3000 cpm/ng) (Pierce). Following extensive dialysis against PBS, over 95 percent of the radioactivity was precipitable by 10 percent TCA. Greater than 98 percent of the $^{125}$I-MB47 bound to a human LDL affinity column. Assays were performed in triplicate in 10×75 mm silicone-coated glass tubes. Increasing concentrations of $^{125}$I-MB47 in 0.1 ml of BSA-barbital buffer were added to 100 ng of pooled, normal human LDL diluted in 0.2 ml of BSA-barbital buffer. Each tube contained 182 fmoles of LDL apo B (assuming an apo B molecular weight of 550,000 daltons). After maintenance for 16 hours at 4 degrees C., LDL was quantitatively precipitated by a lipoprotein depleted rabbit antiserum specific for human LDL. (Only the density greater than 1.21 gm/ml fraction of the rabbit antiserum was used because antibody MB47 binds rabbit apo B.)

Preliminary studies established a concentration of delipidated rabbit antiserum that precipitated 97 percent of 100 ng of $^{125}$I-human LDL. After admixture of the rabbit antibody the tubes were maintained for 16 hours at 4 degrees C., and then spun at 1500 xg for 50 minutes at 4 degrees C. The supernatants were removed, and the pellets were washed twice with 2 ml of ice cold barbital buffer. Nonspecific binding and precipitation were determined in two sets of parallel tubes.

In the first set, no human LDL was added to the initial incubation, but the same amount of rabbit second antibody was added. In the second set of tubes, non-immune rabbit serum (density greater than or equal to 1.21 gm/ml fraction) was substituted for the immune rabbit serum antibody.

Both methods yielded identical values for nonspecific binding, which was linear with increasing concentrations of $^{125}$I-MB47 antibody, and in all cases was less than 1 percent of the total counts added. Specific $^{125}$I-MB47 binding to LDL was obtained by subtracting nonspecific binding from total binding. Binding data were analyzed utilizing a linear regression program for Scatchard analysis of ligand binding systems, that provided an estimate of the antibody affinity constant (Ka) and the receptor or epitope concentration (Munson et al., *Anal. Biochem.*, 107, 220–239 (1980)).

3. Solid Phase-Affixed Antigen RIA

A screening assay to determine whether a hybridoma culture was producing receptors of this invention was performed in flexible round bottom polyvinyl chloride microtiter plates (Dynatech, Inc., Alexandria, Va.) as solid matrix. Lipoprotein antigens (reagent apo B-100) were affixed (bound) to the inner wells of the microtiter plate wells by admixing 0.05 ml of lipoprotein in lipoprotein buffer, and incubating the plates at room temperature for 3 hours to provide a constant final bound antigen concentration, and the solid support. Preliminary direct binding studies using radioiodinated lipoproteins indicated that there were significant differences in the efficiencies with which each of the lipoproteins was bound to the plastic microtiter wells. Therefore, to achieve a final bound antigen concentration of 50 ng of protein/well, VLDL was used at 50 ug/ml, IDL at 6.2 ug/ml, LDL at 4.4 ug/ml, and HDL at 24 ug/ml. Nonspecific binding sites were then blocked by admixing of 0.25 ml of blocking solution in each well, maintaining the admixture for one hour, and then separating the blocking solution from the wells thereby forming a solid support with low nonspecific binding capacity.

For assay, 0.050 ml of antiserum, culture supernatant, or ascites fluid diluted in PBS containing 3 percent BSA, 3 percent normal goat serum, and 0.05 percent Tween-20 [polyoxyethylene (20) sorbitan monolaurate] were admixed in the wells to form solid/liquid phase immunoreaction admixtures. The admixtures were then maintained (immunoreacted) for 18 hours at 4 degrees C.

After washing the wells with PBS containing 3 percent BSA and 0.05 percent Tween-20 to remove nonbound material, solid phase-bound receptors were prepared for direct detection by admixing 10 ng of immunochemically purified and radioiodinated goat anti-murine Ig in each well to form a second solid/liquid phase admixture. This admixture was maintained for 4 hours at 4 degrees C. to allow the labeled second receptors to bind the solid phase-bound first receptors and form a sandwich immunoreactant.

After a final wash to remove nonbound labeled receptors, individual wells were removed and counted for $^{125}$I, the amount of $^{125}$I detected being in direct proportion to the amount of first receptors bound as solid phase immunoreactant.

The immunochemically purified second antibody was radioiodinated enzymatically using immobilized lactoperoxidase and glucose oxidase (Enzymobeads, Bio-Rad Burlingame, Calif.) to specific activities of 3–4 microCi/microgram.

4. Competitive Solid Phase Affixed Receptor RIA

Competitive solid phase radioimmunoassays (RIAs) for human apo B were performed using antibody MB47. Polyvinyl chloride wells were coated with 0.5 ml of human LDL (reagent apo B-100) diluted to 10 ug/ml in PBS, pH 7.35, and maintained for 2 hours at 37 degrees C. Nonspecific binding sites were blocked by coating with 5 percent BSA in PBS for 30 minutes at room temperature. Plates were then washed with PBS washing buffer additionally containing 0.1 percent BSA, 0.01 percent sodium azide and 0.05 percent Tween-20.

Fresh human LDL, prepared from pooled normal plasma, was used as reagent apo B-100 for the standard curve in dilutions ranging from 0.4 ug/ml to 97.2 ug/ml. All dilutions were made in a PBS buffer containing 3 percent BSA, 0.01 percent sodium azide, and 0.05 percent Tween-20. The standard LDL or competitors (0.025 ml) were admixed to the LDL coated wells followed by 0.025 ml of buffer containing a fixed and limiting amount of monoclonal antibody (ascites fluid). The optimal final concentration of antibody was determined from preliminary antibody dilution studies, and was chosen as the amount of antibody resulting in 50 percent of maximum binding.

The plates were maintained for a time period of about 18 hours at 4 degrees C., then washed with the PBS washing buffer. Mouse antibody binding was then quantitated by admixture of 0.05 ml of $^{125}$I-immunopurified goat anti-mouse Ig (450 ng/well, 8,000 cpm/ng). After a 4 hour maintenance time period at 4 degrees C., the plates were washed and individual wells counted.

H. Enzyme-Linked Immunosorbant Assay (ELISA)

1. Noncompetitive ELISA

Isolated MB47 receptors were affixed to the walls of polystyrene microtiter plate wells (Nunc-Immuno Plate I) by admixing 0.15 ml of a sodium bicarbonate buffer pH 9.0, containing 1 ug/ml receptor protein into each well. The wells were maintained for 16 hours at 4 degrees C., and then washed 3 times with PBS containing 0.1 percent BSA and 0.05 percent Tween. Residual nonspecific binding sites were then blocked by admixing 0.2 ml of 3 percent BSA in PBS in each well, maintaining the admixture for 1 hour at 23 degrees C. and then washing as described above. Wells (solid supports) so prepared can be used for up to about one month after preparation, when stored in a humidified chamber.

Reagent apo B-100 (human LDL) was diluted in PBS to concentrations ranging from 2.0 to 0.062 ug/ml for use as standard control solutions. Plasma samples were diluted 1:2000 in PBS.

Fifty microliters of standard or sample were admixed in the wells in triplicate. Within about 5 minutes thereafter, 50 ul of PBS containing mg/ml of HRPO-labeled MB24 receptors were admixed in each well. The immunoreaction admixtures were maintained 30 minutes at 25 degrees C. Nonbound material was then separated from the wells by washing as described before.

The amount of solid phase affixed sandwich immunoreactant containing HRPO label was then assayed by admixing 0.1 ml of freshly prepared substrate solution (distilled water containing 3 percent $H_2O_2$ and 0.67 mg/ml o-phenylenediamine (OPD)) to each well. Color was allowed to develop for 30 minutes at 25 degrees C. The substrate conversion reaction was then stopped by admixing into each well 0.05 ml of 4N $H_2O_2$. The optical density (O.D.) of the solutions was determined at a 490 nanometers (nm) wavelength using a Dynatech MR600 (Dynatech, Alexandria, Va.) microtiter plate reader.

2. Competitive ELISA

Reagent apo B-100 was affixed to the walls of flexible polyvinyl chloride microtiter plate wells (Microtest III, Falcon Labware, Becton, Dickinson & Co., Oxnard, Calif.) as solid matrix by admixing 0.2 ml of PBS containing 5 ug/ml of isolated human LDL into each well. The wells were maintained for 16 hours at 4 degrees C., and were then washed 3 times with 0.2 ml of PBS containing 1 percent BSA, 0.5 percent Tween and 0.02 percent aprotinin (Sigma Chemical Co.). Residual nonspecific binding sites were blocked as described in the noncompetitive ELISA.

For the standard curve, which was included on each plate, the reagent apo B-100 was diluted in PBS containing 0.5 percent lipoprotein-depleted plasma (LPDP) to provide concentrations ranging from 32 mg/ml to 0.25 mg/ml.

Plasma samples were diluted 1:200 in PBS containing 0.5 percent LPDP. Fifty microliters of the standards or samples were admixed in triplicate into the wells. Within about 5 minutes thereafter, 50 ul of PBS containing 3 percent BSA and about 4 ug/ml of MB24 receptors were admixed into each well. The admixtures so formed were maintained for about 18 hours at 4 degrees C. The nonbound material was then separated from the solid phase affixed MB24-reagent apo B-100 immunoreaction products by washing as described above.

The solid phase immunoreactants were prepared for assaying by admixing 0.1 ml of PBS containing 1 percent BSA and an effective amount of HRPO-labeled goat anti-mouse IgG to each well. This second immunoreaction admixture was maintained for about 1 hour at 24 degrees C. and then washed as described above to form a sandwich immunoreactant.

The amount of solid phase affixed sandwich immunoreactant containing HRPO label was assayed as described in the competitive ELISA.

I. Plasma Samples and Lipoprotein Quantification

Plasma samples were obtained from 20 patients with coronary artery disease from the cardiac catheterization laboratory at the San Diego Va. Hospital and from 20 patients with familial hypercholesterolemia from a University of California, San Diego clinic. In addition, plasma was obtained from 20 normal subjects.

Blood was collected into tubes containing 1.5 mg/ml ethylenediamine tetraacetate (EDTA), and the plasma was separated immediately by centrifugation at 4 degrees C.

Total plasma cholesterol and triglycerides were measured on fresh plasma samples in a standardized clinical laboratory using an Abbott ABA-200 bichromatic analyzer, and Boehringer-Mannheim high performance cholesterol reagent 236691 and Abbott Laboratories triglycerides A-gent. LDL- and HDL-cholesterol were measured using techniques described in *Lipid Research Clinic Procedures*, HEW Pub. No. 75-628 (NIH), 2 ed., Washington, D.C., Gov. Print. Off., (1974). Apoprotein B levels were determined using two commercially available radial immunodiffusion kits: Diffugen RID (Tago, Inc., Burlingame, Calif.) which is termed RID #1 here, and M-Partigen RID, (Calbiochem-Behring, La Jolla, Calif.) which is termed RID #2 herein.

J. LDL Binding to a MB47-Sepharose 4B Column

50 Milligrams of substantially pure MB47 receptors, obtained by protein A column chromatography, were linked to 12 ml of cyanogen bromide-activated Sepharose 4B (Pharmacia Fine Chemicals, Piscataway, N.Y.), according to manufacturer's instructions. Subsequently, 10 mg of LDL was added to the column and maintained overnight (about 16 hours) at 4 degrees C. The nonbound LDL was then eluted and assayed for LDL protein as previously described.

The foregoing specification, including the specific embodiments, is intended to be illustrative of the present invention and is not to be taken as limiting. Numerous other variations and modifications can be effected without departing from the true spirit and scope of the novel concepts of the invention.

What is claimed is:

1. A diagnostic assay system in kit form for assaying for the amount of apoprotein B-100 in a body sample comprising:

(a) a first specific binding agent, in an amount sufficient to perform at least one assay, wherein said first specific binding agent specifically binds apoprotein B-100 and is secreted by a hybridoma cell line having ATCC number Hb 8746; and (b) apoprotein B-100 in an amount sufficient to perform at least one assay.

2. The diagnostic assay system of claim 1, wherein said first specific binding agent comprises an intact antibody or an antibody combining site.

3. The diagnostic assay system of claim 1, wherein said first specific binding agent is labeled.

4. The diagnostic assay system of claim 3, wherein said label is selected from the group consisting of enzymes, fluorescent labeling agents, and radiolabeling agents.

5. The diagnostic assay system of claim 1, wherein said first specific binding agent is affixed to a solid matrix.

6. The diagnostic assay system of claim 1, further comprising a labeled second specific binding agent which specifically binds said first specific binding agent, wherein said second specific binding agent is provided in an amount sufficient to perform at least one assay.

7. The diagnostic assay system of claim 6, wherein said second specific binding agent comprises an intact antibody or an antibody combining site.

8. The diagnostic assay system of claim 1, further comprising a second specific binding agent, wherein said second specific binding agent specifically binds apoprotein B-100 at a site other than that bound by the first specific binding agent secreted by HB 8746.

9. The diagnostic assay system of claim 8, wherein said second specific binding agent is secreted by a hybridoma cell line having ATCC number HB 8742.

10. A diagnostic assay system in kit form for assaying for the amount of apoprotein B-100 in a body sample comprising (a) a first specific binding agent which specifically binds apoprotein B-100 and is secreted by a hybridoma cell line having ATCC number HB 8746; and (b) a second specific binding agent which specifically binds apoprotein B-100 at a site other than that bound by the first specific binding agent.

11. The diagnostic assay system of claim 10, wherein said first and second specific binding agents are each provided in an amount sufficient to perform at least one assay.

12. The diagnostic assay system of claim 10, wherein said first and said second specific binding agents comprise intact antibodies or antibody combining sites.

13. The diagnostic assay system of claim 10, wherein said first or said second specific binding agent is labeled.

14. The diagnostic assay system of claim 10, wherein said first or said second specific binding agent is affixed to a solid matrix.

15. A competitive method for assaying apoprotein B-100 in a body fluid sample, comprising:

(a providing a body fluid sample to be assayed;

(b) providing a solid support comprised of a solid matrix having a predetermined amount of apoprotein B-100 affixed thereto;

(c) substantially simultaneously admixing the body fluid sample, the solid support, and a predetermined amount of a first specific binding agent which specifically binds apoprotein B-100 and which is secreted by a hybridoma having ATCC number HB 8746, to form a first solid-liquid phase admixture;

(d) maintaining the admixture under biological assay conditions for a time period sufficient for the first specific binding agent to bind apoprotein B-100 on the solid support and in the body fluid sample, to form a solid phase immunoreactant and a liquid phase immunoreactant;

(e) separating the solid phase immunoreactant from the liquid phase; and (f) determining the amount of first specific binding agent on the solid phase or in the liquid phase.

16. The method of claim 15, wherein said first specific binding agent comprises an intact antibody or an antibody combining site.

17. The method of claim 15, wherein said first specific binding agent is labeled.

18. The method of claim 15, wherein step (f) comprises:

(i) admixing said solid phase immunoreactant with a labeled second specific binding agent which specifically binds said first specific binding agent to form a second solid-liquid phase admixture;

(ii) separating the second solid phase immunoreactant from the second liquid phase; and (iii) determining the amount of labeled second specific binding agent bound to the solid phase.

19. The diagnostic assay system of claim 10, wherein said second specific binding agent is secreted by a hybridoma cell line having ATCC number HB 8742.

* * * * *